United States Patent
Esfandiari et al.

(10) Patent No.: US 10,690,667 B2
(45) Date of Patent: Jun. 23, 2020

(54) RAPID SCREENING ASSAY FOR QUALITATIVE DETECTION OF MULTIPLE FEBRILE ILLNESSES

(71) Applicant: Chembio Diagnostic Systems, Inc., Medford, NY (US)

(72) Inventors: Javanbakhsh Esfandiari, Stony Brook, NY (US); Angelo H. Gunasekera, Mount Sinai, NY (US)

(73) Assignee: Chembio Diagnostic Systems, Inc., Medford, NY (US)

( * ) Notice: Subject to any disclaimer, the term of this patent is extended or adjusted under 35 U.S.C. 154(b) by 18 days.

(21) Appl. No.: 16/124,707

(22) Filed: Sep. 7, 2018

(65) Prior Publication Data

US 2019/0064162 A1    Feb. 28, 2019

Related U.S. Application Data

(63) Continuation of application No. 14/524,451, filed on Oct. 27, 2014, now abandoned.

(51) Int. Cl.
  *G01N 33/569* (2006.01)
  *G01N 33/558* (2006.01)

(52) U.S. Cl.
  CPC ......... *G01N 33/569* (2013.01); *G01N 33/558* (2013.01)

(58) Field of Classification Search
  None
  See application file for complete search history.

(56) References Cited

U.S. PATENT DOCUMENTS

| 3,960,488 A | 6/1976 | Giaever |
| 4,041,146 A | 8/1977 | Giaever |

(Continued)

FOREIGN PATENT DOCUMENTS

| EP | 0299359 | 1/1989 |
| EP | 1284422 | 2/2003 |
| WO | WO 88/08534 | 11/1998 |

OTHER PUBLICATIONS

Chembio Diagnostics, Inc. Form 10-K, Chembio Diagnostics, Inc., Mar. 6, 2014, pp. 1-78; p. 5, third paragraph; p. 29, first paragraph.

(Continued)

*Primary Examiner* — Christopher L Chin
(74) *Attorney, Agent, or Firm* — Gordon & Jacobson, P.C.

(57) ABSTRACT

A single-use multiplex, or assay, screening test for the detection of one or more of a plurality of unrelated febrile illnesses is provided. The febrile illnesses for which the test is designed are unrelated, in that the illnesses may be caused, by way of example, by infection from viruses, bacterium and/or parasites; by infection from viruses, bacterium, parasites or other contagions that are animal borne; by infection from viruses, bacterium, parasites, or other contagions that can be aerosolized for transmission; by infection from viruses, bacterium, parasites or other contagions that are transmitted from direct contact; by infection from viruses, bacterium, parasites or other contagions that are generally transmitted in the tropics and/or subtropics; and/or by infection from a virus, bacteria, parasite sharing one or more related feature and which causes a febrile illness. The assay test provides rapid results to a point of care center or other facility requiring such results to facilitate treatment and or containment of the illnesses.

16 Claims, 10 Drawing Sheets

(56) References Cited

U.S. PATENT DOCUMENTS

| | | |
|---|---|---|
| 4,042,335 A | 8/1977 | Clement |
| 4,059,405 A | 11/1977 | Socickson et al. |
| 4,094,647 A | 6/1978 | Deutsch et al. |
| 4,144,306 A | 3/1979 | Figueras |
| 4,235,601 A | 11/1980 | Deutsch et al. |
| 4,313,734 A | 2/1982 | Leuvering |
| 4,323,536 A | 4/1982 | Columbus |
| 4,361,537 A | 11/1982 | Deutsch et al. |
| 4,366,241 A | 12/1982 | Tom et al. |
| 4,373,932 A | 2/1983 | Gribnau et al. |
| 4,522,786 A | 6/1985 | Ebersole |
| 4,532,107 A | 7/1985 | Siddigi |
| 4,588,555 A | 5/1986 | Provonchee |
| 4,595,654 A | 6/1986 | Reckel et al. |
| 4,632,901 A | 12/1986 | Valkirs et al. |
| 4,668,619 A | 5/1987 | Greenquist et al. |
| 4,703,017 A | 10/1987 | Campbell et al. |
| 4,740,468 A | 4/1988 | Weng et al. |
| 4,770,853 A | 9/1988 | Bernstein |
| 4,786,595 A | 11/1988 | Arai et al. |
| 4,826,759 A | 5/1989 | Guire et al. |
| 4,855,240 A | 8/1989 | Rosenstein et al. |
| 4,857,453 A | 8/1989 | Ullman et al. |
| 4,870,003 A | 9/1989 | Kortright et al. |
| 4,886,742 A | 12/1989 | Kortright et al. |
| 4,906,439 A | 3/1990 | Grenner |
| 4,912,034 A | 3/1990 | Kalra et al. |
| 4,920,046 A | 4/1990 | McFarland et al. |
| 4,943,522 A | 7/1990 | Eisinger et al. |
| 4,956,275 A | 9/1990 | Zuk et al. |
| 4,956,302 A | 9/1990 | Gordon et al. |
| 4,960,691 A | 10/1990 | Gordon et al. |
| 4,960,710 A | 10/1990 | Lau |
| 4,981,785 A | 1/1991 | Nayak |
| 4,981,786 A | 1/1991 | Dafforn et al. |
| 5,004,584 A | 4/1991 | Rayman |
| 5,006,464 A | 4/1991 | Chu et al. |
| 5,006,474 A | 4/1991 | Horstman et al. |
| 5,075,077 A | 12/1991 | Durley, III et al. |
| 5,087,556 A | 2/1992 | Ertinghausen |
| 5,091,153 A | 2/1992 | Bachand |
| 5,104,793 A | 4/1992 | Buck |
| 5,104,811 A | 4/1992 | Berger et al. |
| 5,110,550 A | 5/1992 | Schlipfenbacher |
| 5,132,208 A | 7/1992 | Freitag et al. |
| 5,137,808 A | 8/1992 | Ullman et al. |
| 5,147,780 A | 9/1992 | Pouletty et al. |
| 5,156,952 A | 10/1992 | Litman et al. |
| 5,162,238 A | 11/1992 | Eikmeier et al. |
| 5,169,789 A | 12/1992 | Bernstein |
| 5,173,433 A | 12/1992 | Bachand |
| 5,200,321 A | 4/1993 | Kidwell |
| 5,202,268 A | 4/1993 | Kuhn et al. |
| 5,217,905 A | 6/1993 | Marchand et al. |
| 5,219,762 A | 6/1993 | Katamine et al. |
| 5,223,436 A | 6/1993 | Freitag et al. |
| RE34,312 E | 7/1993 | Geiger et al. |
| 5,232,835 A | 8/1993 | Litman et al. |
| 5,238,649 A | 8/1993 | Nason |
| 5,240,735 A | 8/1993 | Lau |
| 5,244,631 A | 9/1993 | Morikawa |
| 5,244,788 A | 9/1993 | Hubscher |
| RE34,405 E | 10/1993 | Gould et al. |
| 5,275,785 A | 1/1994 | May et al. |
| 5,281,540 A | 1/1994 | Merkh et al. |
| 5,296,192 A | 3/1994 | Carroll et al. |
| 5,300,439 A | 4/1994 | Charlton |
| 5,306,623 A | 4/1994 | Kiser et al. |
| 5,308,775 A | 5/1994 | Donovan et al. |
| 5,332,548 A | 7/1994 | Moore |
| 5,334,502 A | 8/1994 | Sangha |
| 5,338,513 A | 8/1994 | Schlipfenbacher |
| 5,340,748 A | 8/1994 | Baugher et al. |
| 5,356,782 A | 10/1994 | Moorman et al. |
| 5,362,654 A | 11/1994 | Pouletty |
| 5,369,007 A | 11/1994 | Kidwell |
| 5,384,264 A | 1/1995 | Chen et al. |
| 5,391,478 A | 2/1995 | Greene et al. |
| 5,399,316 A | 3/1995 | Yamada |
| 5,411,858 A | 5/1995 | McGeeham et al. |
| 5,415,994 A * | 5/1995 | Imrich ............ B01L 3/5023 435/5 |
| 5,418,136 A | 5/1995 | Miller et al. |
| 5,418,142 A | 5/1995 | Kiser et al. |
| 5,418,167 A | 5/1995 | Matner et al. |
| 5,424,215 A | 6/1995 | Albarella et al. |
| 5,424,220 A | 6/1995 | Goerlach-Graw et al. |
| 5,435,970 A | 7/1995 | Mamenta et al. |
| 5,451,504 A | 9/1995 | Fitzpatrick et al. |
| 5,468,648 A | 11/1995 | Chandler |
| 5,470,713 A | 11/1995 | El Shami et al. |
| 5,474,902 A | 12/1995 | Uylen et al. |
| 5,482,830 A | 1/1996 | Bogart et al. |
| 5,494,830 A | 2/1996 | Hubscher et al. |
| 5,500,350 A | 3/1996 | Baker et al. |
| 5,501,985 A | 3/1996 | Baugher et al. |
| 5,514,557 A | 5/1996 | Moghaddam |
| 5,521,102 A | 5/1996 | Boehringer et al. |
| 5,532,133 A | 7/1996 | Barnewell |
| 5,541,057 A | 7/1996 | Bogart et al. |
| 5,550,063 A | 8/1996 | Bogart |
| 5,552,272 A | 9/1996 | Bogart |
| 5,558,834 A | 9/1996 | Chu et al. |
| 5,559,041 A | 9/1996 | Kang et al. |
| 5,567,594 A | 10/1996 | Calenoff |
| 5,571,667 A | 11/1996 | Chu et al. |
| 5,591,645 A | 1/1997 | Rosenstein |
| 5,602,040 A | 2/1997 | May et al. |
| 5,604,105 A * | 2/1997 | Jackowski ......... C07K 16/4283 435/7.4 |
| 5,604,110 A | 2/1997 | Baker et al. |
| 5,607,863 A | 3/1997 | Chandler |
| 5,616,467 A | 4/1997 | Olsen et al. |
| 5,620,845 A | 4/1997 | Gould et al. |
| 5,622,871 A * | 4/1997 | May ............... G01N 33/548 436/514 |
| 5,624,809 A | 4/1997 | Skold et al. |
| 5,629,164 A | 5/1997 | Rivers |
| 5,629,214 A | 5/1997 | Crosby |
| 5,639,671 A | 6/1997 | Bogart et al. |
| 5,641,639 A | 6/1997 | Perry |
| 5,648,274 A | 7/1997 | Chandler |
| 5,656,503 A | 8/1997 | May et al. |
| 5,658,801 A | 8/1997 | Poissant et al. |
| 5,670,381 A | 9/1997 | Jou et al. |
| 5,686,315 A | 11/1997 | Pronovost |
| 5,695,928 A | 12/1997 | Stewart et al. |
| 5,695,930 A | 12/1997 | Weinstein et al. |
| 5,710,005 A | 1/1998 | Rittenburg |
| 5,714,341 A | 2/1998 | Thieme et al. |
| 5,714,389 A | 2/1998 | Charlton et al. |
| 5,723,345 A | 3/1998 | Yamauchi et al. |
| 5,726,010 A | 3/1998 | Clark |
| 5,728,587 A | 3/1998 | Kang et al. |
| 5,739,041 A | 4/1998 | Nazareth et al. |
| 5,750,333 A | 5/1998 | Clark |
| 5,766,961 A | 6/1998 | Pawlak et al. |
| 5,766,962 A | 6/1998 | Childs et al. |
| 5,770,460 A | 6/1998 | Pawlak et al. |
| 5,773,234 A | 6/1998 | Pronovost et al. |
| 5,786,220 A | 7/1998 | Pronovost et al. |
| 5,798,273 A | 8/1998 | Shuler et al. |
| 5,807,756 A | 9/1998 | Bauman et al. |
| 5,814,522 A | 9/1998 | Zimmer et al. |
| 5,824,268 A | 10/1998 | Bernstein et al. |
| 5,827,646 A | 10/1998 | Middeldorp et al. |
| 5,846,838 A | 12/1998 | Chandler |
| 5,853,670 A | 12/1998 | Bunce |
| 5,861,265 A | 1/1999 | Perry |
| 5,869,272 A | 2/1999 | Bogart et al. |
| 5,869,345 A | 2/1999 | Chandler |
| 5,872,713 A | 2/1999 | Douglas et al. |
| 5,874,216 A | 2/1999 | Mapes |
| 5,877,028 A | 3/1999 | Chandler et al. |

(56) References Cited

U.S. PATENT DOCUMENTS

| | | |
|---|---|---|
| 5,879,951 A | 3/1999 | Sy |
| 5,885,526 A | 3/1999 | Chu |
| 5,885,527 A | 3/1999 | Buechler |
| 5,891,650 A | 4/1999 | Godowski et al. |
| 5,900,379 A | 5/1999 | Noda et al. |
| 5,902,722 A | 5/1999 | Di Cesare et al. |
| 5,912,116 A | 6/1999 | Caldwell |
| 5,922,533 A | 7/1999 | Vallari et al. |
| 5,922,615 A | 7/1999 | Nowakowski et al. |
| 5,939,252 A | 8/1999 | Lennon et al. |
| 5,939,272 A | 8/1999 | Buechler et al. |
| 5,948,695 A | 9/1999 | Douglas et al. |
| 5,955,377 A | 9/1999 | Maul et al. |
| 5,958,790 A | 9/1999 | Cerny |
| 5,965,458 A | 10/1999 | Kouvonen et al. |
| 5,972,720 A | 10/1999 | Nichtl et al. |
| 5,976,895 A | 11/1999 | Cipkowski |
| 5,985,675 A | 11/1999 | Charm et al. |
| 5,989,921 A | 11/1999 | Charlton et al. |
| 5,998,220 A | 12/1999 | Chandler |
| 5,998,221 A | 12/1999 | Malick et al. |
| 6,008,056 A | 12/1999 | Thieme |
| 6,017,767 A | 1/2000 | Chandler |
| 6,027,890 A | 2/2000 | Ness et al. |
| 6,040,195 A | 3/2000 | Carroll et al. |
| 6,046,013 A | 4/2000 | Tidey et al. |
| 6,046,057 A | 4/2000 | Nazareth et al. |
| 6,057,166 A | 5/2000 | Childs et al. |
| 6,060,326 A | 5/2000 | Frank et al. |
| 6,063,337 A | 5/2000 | Markart |
| 6,087,184 A | 7/2000 | Magginetti et al. |
| 6,106,732 A | 8/2000 | Johnston et al. |
| 6,140,134 A | 10/2000 | Rittenburg |
| 6,140,136 A | 10/2000 | Lee |
| 6,168,956 B1 | 1/2001 | Chandler |
| 6,187,268 B1 | 2/2001 | Albarella et al. |
| 6,187,598 B1 | 2/2001 | May et al. |
| 6,194,220 B1 | 2/2001 | Malick et al. |
| 6,197,494 B1 | 3/2001 | Oberhardt |
| 6,221,625 B1 | 4/2001 | Ashihara et al. |
| 6,221,678 B1 | 4/2001 | Chandler |
| 6,224,831 B1 | 5/2001 | Stafford et al. |
| 6,228,660 B1 | 5/2001 | May et al. |
| 6,235,464 B1 | 5/2001 | Henderson et al. |
| 6,248,598 B1 | 6/2001 | Bogema |
| 6,258,548 B1 | 7/2001 | Buck |
| 6,271,040 B1 | 8/2001 | Buechler |
| 6,271,045 B1 | 8/2001 | Douglas et al. |
| 6,271,046 B1 | 8/2001 | Chandler |
| 6,277,650 B1 | 8/2001 | Nazareth et al. |
| 6,284,550 B1 | 9/2001 | Carroll et al. |
| 6,287,875 B1 | 9/2001 | Geisberg |
| 6,297,020 B1 | 10/2001 | Brock |
| 6,297,060 B1 | 10/2001 | Nowakowski et al. |
| 6,300,142 B1 | 10/2001 | Andrewes et al. |
| RE37,437 E | 11/2001 | Friesen et al. |
| 6,316,205 B1 | 11/2001 | Guan et al. |
| 6,316,264 B1 | 11/2001 | Corey et al. |
| 6,319,676 B1 | 11/2001 | Nazareth et al. |
| 6,326,214 B1 | 12/2001 | Liu et al. |
| 6,335,205 B1 | 1/2002 | Bausback |
| 6,352,862 B1 | 3/2002 | Davis et al. |
| 6,362,008 B1 | 3/2002 | Kohn et al. |
| 6,368,875 B1 | 4/2002 | Geisberg |
| 6,368,876 B1 | 4/2002 | Huang et al. |
| 6,372,514 B1 | 4/2002 | Lee |
| 6,372,515 B1 | 4/2002 | Casterlin et al. |
| 6,372,516 B1 | 4/2002 | Sun |
| 6,376,195 B1 | 4/2002 | Mapes |
| 6,399,398 B1 | 6/2002 | Cunningham et al. |
| 6,403,383 B1 | 6/2002 | Casterlin et al. |
| 6,403,384 B1 | 6/2002 | Lea |
| 6,406,922 B2 | 6/2002 | Casterlin et al. |
| 6,413,473 B1 | 7/2002 | Bacon |
| 6,413,784 B1 | 7/2002 | Lundsgaard et al. |
| 6,436,722 B1 | 8/2002 | Clark et al. |
| 6,455,324 B1 | 9/2002 | Douglas |
| 6,472,226 B1 | 10/2002 | Barradine et al. |
| 6,475,805 B1 | 11/2002 | Charm et al. |
| 6,485,982 B1 | 11/2002 | Charlton |
| 6,489,129 B1 | 12/2002 | Faatz et al. |
| 6,492,127 B2 | 12/2002 | Goodell et al. |
| 6,500,629 B1 | 12/2002 | Cleaver et al. |
| 6,503,702 B1 | 1/2003 | Stewart |
| 6,503,722 B1 | 1/2003 | Valkirs |
| 6,511,814 B1 | 1/2003 | Carpenter |
| 6,514,769 B2 | 2/2003 | Lee |
| 6,514,773 B1 | 2/2003 | Klein et al. |
| 6,528,321 B1 | 3/2003 | Fitzgerald et al. |
| 6,528,322 B1 | 3/2003 | Carlsson et al. |
| 6,528,323 B1 | 3/2003 | Thayer et al. |
| 6,528,325 B1 | 3/2003 | Hubscher et al. |
| 6,534,324 B1 | 3/2003 | Zin |
| 6,544,474 B2 | 4/2003 | Douglas |
| 6,548,309 B1 | 4/2003 | Moore et al. |
| 6,551,842 B1 | 4/2003 | Carpenter |
| 6,592,815 B1 | 7/2003 | Zimmer |
| 6,593,085 B1 | 7/2003 | Barnett et al. |
| 6,602,719 B1 | 8/2003 | Carpenter |
| 6,617,116 B2 | 9/2003 | Guan et al. |
| 6,623,955 B2 | 9/2003 | Matner et al. |
| 6,627,459 B1 | 9/2003 | Tung et al. |
| 6,632,681 B1 | 10/2003 | Chu |
| 6,632,842 B2 | 10/2003 | Chaudry et al. |
| 6,645,732 B2 | 11/2003 | Faatz et al. |
| 6,649,418 B1 | 11/2003 | Geisberg |
| 6,656,744 B2 | 12/2003 | Pronovost et al. |
| 6,656,745 B1 | 12/2003 | Cole |
| 6,660,469 B1 | 12/2003 | Wright et al. |
| 6,663,833 B1 | 12/2003 | Stave et al. |
| 6,673,628 B2 | 1/2004 | Freitag et al. |
| RE38,430 E | 2/2004 | Rosenstein |
| 6,686,167 B2 | 2/2004 | Bagaria |
| 6,699,722 B2 | 3/2004 | Bauer et al. |
| 6,703,196 B1 | 3/2004 | Klepp et al. |
| 6,706,539 B2 | 3/2004 | Nelson et al. |
| 6,713,309 B1 | 3/2004 | Anderson et al. |
| 6,727,073 B1 | 4/2004 | Moore et al. |
| 6,737,277 B1 | 5/2004 | Kang et al. |
| 6,750,031 B1 | 6/2004 | Ligler et al. |
| 6,753,190 B1 | 6/2004 | Okada et al. |
| 6,767,710 B2 | 7/2004 | DiNello et al. |
| 6,767,714 B2 | 7/2004 | Nazareth et al. |
| 6,780,651 B2 | 8/2004 | Douglas et al. |
| 6,790,611 B2 | 9/2004 | Lassen et al. |
| 6,797,481 B1 | 9/2004 | Ullman et al. |
| 6,808,889 B2 | 10/2004 | Fitzpatrick et al. |
| 6,808,937 B2 | 10/2004 | Ligler et al. |
| 6,812,038 B1 | 11/2004 | Mendel-Hartgvig et al. |
| 6,818,180 B2 | 11/2004 | Douglas et al. |
| 6,818,455 B2 | 11/2004 | May et al. |
| 6,824,975 B2 | 11/2004 | Hubscher et al. |
| 6,824,997 B1 | 11/2004 | Moore et al. |
| 6,828,110 B2 | 12/2004 | Lee et al. |
| RE38,688 E | 1/2005 | Friesen et al. |
| 6,844,200 B2 | 1/2005 | Brock |
| 6,846,635 B1 | 1/2005 | Anderson et al. |
| 6,849,414 B2 | 2/2005 | Guan et al. |
| 6,855,561 B2 | 2/2005 | Jerome et al. |
| 6,863,866 B2 | 3/2005 | Kelly et al. |
| 6,867,051 B1 | 3/2005 | Anderson et al. |
| 6,887,701 B2 | 5/2005 | Anderson et al. |
| 6,905,835 B2 | 6/2005 | Sorell Gomez et al. |
| 6,924,153 B1 | 8/2005 | Boehringer et al. |
| 6,927,068 B2 | 8/2005 | Simonson et al. |
| 6,991,940 B2 | 1/2006 | Carroll et al. |
| 7,018,847 B2 | 3/2006 | Mendel-Hartvig et al. |
| 7,045,342 B2 | 5/2006 | Nazareth et al. |
| 7,049,130 B2 | 5/2006 | Carroll et al. |
| 7,109,042 B2 | 9/2006 | May et al. |
| 7,189,522 B2 | 3/2007 | Esfandiari |
| 7,569,397 B2 | 8/2009 | Esfandiari |
| 7,682,801 B2 | 3/2010 | Esfandiari |
| 7,879,597 B2 | 2/2011 | Esfandiari |

(56) References Cited

U.S. PATENT DOCUMENTS

| | | | |
|---|---|---|---|
| 8,404,493 B2* | 3/2013 | Fong | G01N 33/558 422/400 |
| 8,507,259 B2 | 8/2013 | Esfandiari | |
| 8,877,450 B2 | 11/2014 | Esfandiari | |
| 2001/0012637 A1 | 8/2001 | Casterlin et al. | |
| 2001/0026942 A1 | 10/2001 | Carpenter et al. | |
| 2001/0026944 A1 | 10/2001 | Chung et al. | |
| 2001/0034068 A1 | 10/2001 | Spivey et al. | |
| 2001/0039057 A1 | 11/2001 | Douglas et al. | |
| 2001/0048893 A1 | 12/2001 | Norris et al. | |
| 2002/0001853 A1 | 1/2002 | Obremski et al. | |
| 2002/0015663 A1 | 2/2002 | Goldstein et al. | |
| 2002/0019062 A1 | 2/2002 | Lea et al. | |
| 2002/0031839 A1 | 3/2002 | McNeirney et al. | |
| 2002/0046614 A1 | 4/2002 | Alley | |
| 2002/0048819 A1 | 4/2002 | Alley | |
| 2002/0052050 A1 | 5/2002 | Douglas et al. | |
| 2002/0057991 A1 | 5/2002 | Kelly et al. | |
| 2002/0058330 A1 | 5/2002 | Carroll et al. | |
| 2002/0110803 A1 | 8/2002 | Dhar et al. | |
| 2002/0119497 A1 | 8/2002 | Wild et al. | |
| 2002/0142291 A1 | 10/2002 | Bauer et al. | |
| 2002/0155028 A1 | 10/2002 | Wong | |
| 2002/0172937 A1 | 11/2002 | Dave et al. | |
| 2002/0173050 A1 | 11/2002 | DiNello et al. | |
| 2002/0192839 A1 | 12/2002 | Mink et al. | |
| 2003/0045001 A1 | 3/2003 | Burgess et al. | |
| 2003/0118480 A1 | 6/2003 | Kaylor | |
| 2003/0124740 A1 | 7/2003 | Bachand | |
| 2003/0138351 A1 | 7/2003 | Etes et al. | |
| 2003/0143639 A1 | 7/2003 | Matsushita et al. | |
| 2003/0170613 A1 | 9/2003 | Straus | |
| 2003/0180967 A1 | 9/2003 | Shigetoh | |
| 2003/0191151 A1 | 10/2003 | Chaudry et al. | |
| 2004/0087036 A1 | 5/2004 | Chung et al. | |
| 2004/0142495 A1 | 7/2004 | Hartman et al. | |
| 2004/0161859 A1 | 8/2004 | Guo et al. | |
| 2004/0184954 A1 | 9/2004 | Guo et al. | |
| 2004/0219694 A1 | 11/2004 | Chittock et al. | |
| 2004/0235189 A1 | 11/2004 | Lu | |
| 2004/0241779 A1 | 12/2004 | Piasio et al. | |
| 2004/0248322 A1 | 12/2004 | Charlton | |
| 2005/0074900 A1 | 4/2005 | Morgan et al. | |
| 2005/0079629 A1 | 4/2005 | Guo et al. | |
| 2005/0112779 A1 | 5/2005 | Wei et al. | |
| 2005/0112780 A1 | 5/2005 | Song | |
| 2005/0112782 A1 | 5/2005 | Buechler | |
| 2005/0130293 A1 | 6/2005 | Blatt et al. | |
| 2005/0130319 A1 | 6/2005 | Biegelsen et al. | |
| 2005/0136500 A1 | 6/2005 | Yang et al. | |
| 2005/0142032 A1 | 6/2005 | Hoenes et al. | |
| 2005/0164404 A1 | 7/2005 | Marlborugh et al. | |
| 2005/0170527 A1 | 8/2005 | Boehringer et al. | |
| 2005/0208677 A1 | 9/2005 | Owens et al. | |
| 2005/0227371 A1 | 10/2005 | Gokhan | |
| 2005/0244985 A1 | 11/2005 | Freitag et al. | |
| 2005/0244986 A1 | 11/2005 | May et al. | |
| 2006/0099719 A1 | 5/2006 | Curcio | |
| 2006/0121626 A1 | 6/2006 | Imrich | |
| 2006/0134803 A1 | 6/2006 | Esfandiari | |
| 2007/0020768 A1 | 1/2007 | Rundstrom et al. | |
| 2007/0059203 A1 | 3/2007 | Burrell | |
| 2008/0318341 A1 | 12/2008 | Esfandiari | |
| 2009/0148933 A1 | 6/2009 | Battrell et al. | |
| 2009/0181411 A1 | 7/2009 | Battrell | |
| 2011/0151584 A1 | 6/2011 | Esfandiari | |
| 2012/0282154 A1 | 11/2012 | Slowey et al. | |
| 2013/0130262 A1 | 5/2013 | Battrell | |
| 2016/0116446 A1 | 4/2016 | Esfandiari | |

OTHER PUBLICATIONS

The Globalization of Leptospirosis; Worldwide Incidence Trends, Pappas G. et al., International Journal of Infectious Diseases. 2008, vol. 12, pp. 351-357; p. 355, third paragraph. DOI: 10.1016/j.ijid/2007.09.011.
Just the Facts . . . Scrub Typhus, U.S. Army Public Health Command, Entomological Sciences Program, Jan. 2010, pp. 1-2; p. 1, first paragraph.
Multiplexed Point-of-Care Test for Acute Febrile Illness (mPOCT), THSTI, World Health Organization Candidate Demonstration Project Proposal, Jan. 14, 2014, pp. 1-11; p. 1, first paragraph; p. 2 paragraph continued from p. 1—second paragraph; p. 3, first paragraph; p. 4, Epidemiology Table.
Prevalence of Bacterial Febrile Illnesses in Children in Kilosa District, Tanzania, Chipwaza, B. et al., PLOS Neglected Tropical Diseases, May 8, 2015, pp. 1-18; p. 3, second paragraph; p. 15, second paragraph. DOI: 10.1371/journal/pntd.0003750.
Rare Concurrent Infection with Scrub Typhus, Dengue and Malaria in a Young Female, Kumar, S. et al., J Vector Borne Dis 51, Mar. 2014, pp. 71-72; p. 72, first paragraph.
P24, A printout from http://en.wikipedia.org/wiki/P24 retrieved on Oct. 2, 2012.
"An Integrated Microfluidic Biomechanical Detection system for Protein Analysis With Magnetic Bead-Based Sampling Capabilities" Choi et al., Lab Chip, 2002, 2 pp. 27-30.
"Testing for p24 Antigen," Centers for Disease Control and Prevention. Model Performance Evaluation Program. Human Immunodeficiency Virus Type (1 (HIV-1), 2002.
HIV-1 Gag p24, BioAcademia, 2006, available at http://www.bioacademia.co.jp/en/product_list.php?srch_keyword=HIV-1+Gag+p24.
Human Immunodeficiency Virus Type 1 Gag p24 Alters the Composition of Immunoproteasomes and Affects Antigen Presentation, Steers et al., Journal of Virology, Apr. 24, 2009.
Targeting to Compartments of the Endomembranesystem for the Accumulation of HIV-1 p24 Intobacco Plants, Lopez et al., 2008.

* cited by examiner

READ THE RESULTS AT 20 MINUTES
NEGATIVE RESULT· ONE LINE OR POSTIVE
RESULT INDICATES PRESENCE OF ANTIGEN
OR ANTIGENS (TWO-SIX LINES)

NEGATIVE RESULT

READ THE RESULTS AT 20 MINUTES
NEGATIVE RESULT: ONE LINE OR POSTIVE
RESULT INDICATES PRESENCE OF ANTIGEN
OR ANTIGENS (TWO-SIX LINES)

POSITIVE RESULT

READ THE RESULTS AT 20 MINUTES
NEGATIVE RESULT: ONE LINE OR POSTIVE
RESULT INDICATES PRESENCE OF ANTIGEN
OR ANTIGENS (TWO-SIX LINES)

POSITIVE RESULT

RAPID SCREENING ASSAY FOR QUALITATIVE DETECTION OF MULTIPLE FEBRILE ILLNESSES

CROSS-REFERENCE TO RELATED APPLICATION

This application is a continuation of U.S. application Ser. No. 14/524,451, filed Oct. 27, 2014, the contents of which are hereby incorporated by reference herein in their entirety.

BACKGROUND OF THE INVENTION

1. Field of the Invention

The present invention relates to immunochromatographic, rapid screening test for the in vitro detection of illnesses from a bodily fluid, including, but not limited to, blood. More particularly, the test is a qualitative assay test for the quick screening of multiple febrile illnesses from the bodily fluid.

2. State of the Art

A sudden and often severe fever is indicative of a febrile illness. In many parts of the world, febrile illnesses are often misdiagnosed due to the inherent variability associated with febrile-related diseases. Misdiagnosis is followed by presumptive treatment which may not address the causative infection. Improper treatment and control may allow infectious febrile illnesses to spread through populations. Febrile illnesses with potentially high morbidity and mortality include but are not limited to Ebola, Malaria, Dengue fever, Plague, and Melioidosis.

Ebola, previously known as Ebola hemorrhagic fever, is a rare and deadly disease caused by infection with one of the Ebola virus strains. Ebola can cause disease in humans and nonhuman primates (monkeys, gorillas, and chimpanzees). Ebola is caused by infection with a virus of the family Filoviridae, genus Ebolavirus. There are four identified Ebola virus species known to cause disease in humans: Ebola virus (Zaire ebolavirus); Sudan virus (Sudan ebolavirus); Taï Forest virus (nil Forest ebolavirus, formerly Cote d'Ivoire ebolavirus); and Bundibugyo virus (Bundibugyo ebolavirus). Researchers believe that the virus is animal-borne and that bats are the most likely reservoir. Transmission occurs through direct contact with blood or other body fluids, objects contaminated with the virus and infected animals. Early symptoms such as fever are non-specific and often seen in patients with other illnesses, including, e.g., Malaria.

Malaria results from infection with the parasite *Plasmodium*. The *Plasmodium* parasite is transmitted via the bite of an infected *Anopheles* mosquito. The infected mosquito deposits parasites onto its human host, which then invade the host's liver followed by the red blood cells. The rupturing of infected red blood cells release parasites into the blood stream, giving rise to Malaria symptoms such as nausea, fever, vomiting, headache, sweating, and chills. These flu-like symptoms can be mild, severe, or even fatal.

The Dengue virus is a single-stranded RNA virus from the Flaviviridae family that can cause Dengue Fever, Dengue hemorrhagic fever, and/or Dengue shock syndrome. Dengue is considered to be one of the leading causes of illness in tropical and subtropical regions. It is estimated that nearly 100 million people are infected with Dengue on an annual basis. Dengue fever, the most common presentation of infection with Dengue virus, is caused by any of the four Dengue serotypes (Dengue 1, 2, 3, or 4). Transmission is carried out by the mosquito vectors *Aedes aegypti* and *Aedes albopictus*.

Infection with the gram-negative bacterium *Burkholderia pseudomallei* often presents as the tropical disease Melioidosis, also known as Whitmore's disease, which is found primarily in Southeast Asia and Australia. The bacteria are spread through direct contact with or inhalation of contaminated water or soil. Localized, pulmonary, bloodstream, or disseminated infection can occur and symptoms, such as fever, pain, ulceration, cough, respiratory distress, weight loss, headache, or seizures, generally appear two to four weeks after exposure. However, there are indications that the bacteria may remain latent in a host for up to several years. The infection, characterized most often by the CPS antigen, can be treated with appropriate antimicrobial therapy when diagnosed properly. Due to the severity of illness and its aerosol transmission, there is concern regarding the use of *Burkholderia pseudomallei* as a bioterrorism agent.

*Yersinia pestis* is a gram negative, rod-shaped bacterium that results in Plague. It is found in rodents and their fleas, and occurs in many parts of the world including the United States. Historically, three large pandemics have killed approximately 200 million people. While large outbreaks are now rare, a few cases of plague still arise in endemic areas around the world including the southwestern region of the United States. There are three forms of plague: pneumonic, bubonic and septicemic plague. Bubonic plague is the most common, while pneumonic plague is considered to be the most likely to be encountered in a bioterrorism event. The pneumonic form of the disease occurs when *Yersinia pestis* infects the lungs. It can be transmitted through the air when a person breathes in aerosolized bacteria. With pneumonic plague, the first signs of illness are fever, headache, weakness and a rapidly developing pneumonia. The pneumonia progresses for 2 to 4 days and may cause respiratory failure and shock. To reduce the likelihood of death, antibiotics must be administered within the first 24 hours; thus, early diagnosis is essential.

All of the above illnesses are non-specifically characterized by a high grade fever.

Many types of ligand-receptor assays have been used to detect the presence of various substances that are indicative of a bodily response to an illness state. Such substances, often generally called ligands, are present in body fluids such as blood, urine, or saliva. These assays involve antigen antibody reactions, synthetic conjugates comprising radioactive, enzymatic, fluorescent, or visually observable polystyrene or metal sol tags, and specially designed chambers in which the antigens and antibodies react. In all these assays, there is a receptor, e.g., an antibody, which is specific for the selected ligand or antigen, and a means for detecting the presence, and in some cases the amount, of the ligand-receptor reaction product. Some tests are designed to make a quantitative determination, but in many circumstances all that is required is a positive/negative qualitative indication. A visually observable indicator such as the presence of agglutination or a color change is preferred.

Even the qualitative assays must be very sensitive because of the often small concentration of the ligand of interest in the test fluid. False positives can also be troublesome, particularly with agglutination and other rapid detection methods such as dipstick and color change tests. Because of these problems, so-called "sandwich" assays and other sensitive detection mechanisms which use metal sols or other types of colored particles have been developed.

In a "sandwich" assay, a target analyte such as an antigen is "sandwiched" between a labeled antibody and an antibody immobilized onto a solid support. The assay is read by observing the presence and/or amount of bound antigen-labeled antibody complex. In a "competition" immunoassay, antibody bound to a solid surface is contacted with a sample containing an unknown quantity of antigen analyte and with labeled antigen of the same type. The amount of labeled antigen bound on the solid surface is then determined to provide an indirect measure of the amount of antigen analyte in the sample.

Because these and other assays can detect both antibodies and antigens, they are generally referred to as immunochemical ligand-receptor assays or simply immunoassays.

Solid phase immunoassay devices, whether of the sandwich or competition type, provide sensitive detection of an analyte in a biological fluid sample such as blood, urine, or saliva. Solid phase immunoassay devices incorporate a solid support to which one member of a ligand-receptor pair, usually an antibody, antigen, or hapten, is bound. Common early forms of solid supports were plates, tubes, or beads of polystyrene which were well known from the fields of radioimmunoassay and enzyme immunoassay. More recently, a number of porous materials such as nylon, nitrocellulose, cellulose acetate, glass fibers, and other porous polymers have been employed as solid supports.

A number of self-contained immunoassay kits using porous materials as solid phase carriers of immunochemical components such as antigens, haptens, or antibodies have been described. These kits are usually dipstick, flow-through, or migratory in design. One test kit is disclosed in co-owned U.S. Pat. No. 7,879,597 to Esfandiari which is hereby incorporated by reference herein in its entirety. This reference teaches an accurate self-contained immunoassay that can be used by minimally trained personnel to obtain valid qualitative assay results. The test also requires a relatively small amount of ligand molecule and can be manufactured at low cost. In addition, the test can be operated in a sensitive manner with a small sample volume while providing accurate results.

SUMMARY

Early and appropriate diagnosis of febrile illnesses and infection may allow for effective treatment options against associated complications and may also prevent transmission of the diseases.

A single-use multiplex, or assay, screening test for the detection of febrile illnesses is provided. The febrile illness assay test is intended for use as a point-of-care device to aid in the diagnosis of several severe febrile illnesses using a body fluid such a fingerstick whole blood. The assay test provides relatively quick results and facilitates clinical decision making.

According to one aspect, the early manifestation of many febrile diseases is very similar. Accordingly, a multiplex assay that can distinguish among febrile diseases at an early stage can enable a more efficient rapid response.

The assay test is an in vitro qualitative detection test preferably utilized for the presumptive detection of infection with one or more of various febrile illnesses, i.e., to detect ("positive") or reject ("negative") the illnesses.

In one embodiment, the assay test is adapted to provide presumptive (i.e., confirmatory) detection of at least two unrelated febrile illnesses. In one embodiment, the assay test is adapted to provide presumptive detection of at least three unrelated febrile illnesses. The febrile illnesses can be selected for testing on the assay using common features of (or alternatively dissimilar features relative to) the two or more of the unrelated febrile illnesses. By way of example, the selection of febrile illnesses for which the test is designed may include illnesses caused by one or more of the following: viruses, bacterium and/or parasites (different pathogens); viruses, bacterium, parasites or other contagions that are animal borne, whether selected to be animal borne by the same animal (mosquitoes) or by different animals (e.g., bat, rodent, mosquito, flea); viruses, bacterium, parasites, or other contagions that can be aerosolized for transmission; viruses, bacterium, parasites or other contagions that are transmitted from direct contact; viruses, bacterium, parasites or other contagions that are generally transmitted in the tropics and/or subtropics; virus, bacteria, parasite sharing one or more related features and which causes a febrile illness.

It is specifically recognized that the febrile illnesses tested by the assay test do not share any particularly common cause for their respective disease states. That is, the positive detection of one febrile illness is not presumptive, indicative or otherwise suggestive of testing positive for a second febrile illness which is the subject of the assay test. Febrile illnesses under the test are epidemiologically independent; i.e., are known to have different etiologies. That is, there is no known pattern, causation, or other relationship from one illness to the other because each results from at least a different pathogen. As such, to the extent the test provides a positive detection for one febrile illness, it is expected that only one positive detection for a febrile illness will be indicated on any one test. It is, of course, possible that a test sample can provide positive detection of two or even more febrile illnesses. But given the lack of relationship of the febrile illnesses for which the test is administered, such results would not be expected. Nonetheless, it is anticipated that the unrelated febrile illnesses for which any test is designed will have a rationale in their selection for inclusion together on a test.

In accord with one aspect of the assay test, the febrile illnesses detectable by the assay test may be linked by those febrile illnesses having a prevalence within a geographical proximity (by of example, within a state, or within a country, or within neighboring countries, or within proximate countries, or within a continent, or within 20° latitude of the equator, or as bounded by geological formations including rivers and/or mountains and/or valleys, or subject to environmental disaster, or geopolitical hardships, or other geographically definable boundary), and/or those febrile illnesses having a prevalence within a population in a given time period, and/or those febrile illnesses to which a group or population may be subject (by way of example, general population of western Africa, or aid workers of one or more relief organizations, whether localized or scattered, or inhabitants of one or more temporary or semi-permanent shelter or housing systems, including shelter or housing established by the United Nations or another relief aid organization), and/or those febrile illnesses which are potentially borne by travelers at a point of entry at a geographical location (e.g., air travelers at an airport arriving from selected points of origination or going to selected points of destination, or similar sea travelers at a sea port). For each of the potential groups identified above, an assay test may be designed to test for febrile illnesses that are appropriate for the circumstance.

By way of example, the febrile illnesses detected can include Ebola Virus (viral infection and animal borne), *Plasmodium* parasites (Malaria)(parasitic infection and animal borne by mosquito), Dengue virus (viral infection, animal borne by mosquito, and tropical/subtropical), *Yersinia pestis* (Plague)(bacterial infection, animal borne by rodent and their fleas, specific endemic regions, can be in aerosol form), *Burkholderia pseudomallei* (Melioidosis) (bacterial infection, tropical illness, can be in aerosol form or in contaminated soil). Other febrile illnesses that may be tested for include, by way of example, Anthrax, Lassa fever, Marburg hemorrhagic Fever, Leptospirosis, Rickettsial disease, Tularemia, Thyphoid, Chikungunya, *Coxiella burnetii* bacteria (Q-fever), Meningococcal, Pneomococcus, and Crimean-Congo haemorrhagic fever (CCHF).

In accord with embodiments of the assay, and not by way of limitation, the assay is adapted to detect for at least three of, or all of, Ebola Virus, *Plasmodium* parasites (Malaria), Dengue virus, as well as the bacteria *Yersinia pestis* (Plague) and *Burkholderia pseudomallei* (Melioidosis) in a bodily fluid. In accord with one embodiment of the assay test, the assay is adapted to use the bodily fluid of fingerstick whole blood, venous whole blood, serum and/or plasma. In one aspect, these febrile illnesses are chosen to be part of a single assay because of their potential use in bioterrorism.

In accord with an embodiment, the febrile illness assay test includes at least one lateral flow sorbent material test strip having a first width and a first length substantially longer than said first width, and defining a lateral flow pathway along its length. A test site is provided on or in the test strip with distinct test lines, each comprising a ligand-binding protein or particle adapted to couple with an antigen (antibody) of a distinct one of the febrile illnesses under test. Spaced apart from the test site are a plurality of conjugates adapted to combine with an antigen (or antibody) of the respective febrile illnesses under test. The conjugates include colloidal gold dye particles, and are bound to the test strip in a solid phase. Ligand binding proteins and their conjugates for use in a test cell are described in U.S. Pat. No. 5,714,389 to Charlton, the teaching of which is hereby incorporated by reference herein in its entirety. The test strip is provided in a housing, and includes a clear test window over a testing area under which results of the tests are displayed. An optionally diluted sample (sample and buffer) is applied to the test strip and allowed to flow across the test lines. The antibodies (or antigens), if any, in the sample laterally flow to the test site and combine with the antigens (or antibodies) immobilized at the respective test lines. The conjugates are also released from the test strip and caused to laterally flow to the test site. The conjugates are captured by antibodies (or antigens) of the febrile illnesses which are retained at the respective test lines. In a positive test, a conjugated antigen (or antibody) migrates along the test strip and is captured by its respective antigen-bound antibody at one of the test lines, producing a visible, colored line to positively indicate a febrile illness. The test lines are keyed to indicate which febrile illness is associated with each test line. It is appreciated that the test may be indicative of one or more febrile illnesses, on the showing of one or more colored lines at the test site. In the absence of the antibodies (or antigens) indicative of the febrile illnesses of interest, no associated colored line would be observed under the test window area.

In accord with one embodiment of the assay test, the assay test includes a first sorbent material having a first location for receiving a buffer solution (in the case of a dry conjugate system) or a conjugate solution (in the case of a liquid conjugate system) with the first sorbent material defining a first horizontal flow path, a second sorbent material having a second location for receiving a sample with the second sorbent material defining a second horizontal flow path distinct from the first flow path, and a plurality of longitudinally displaced test lines or test sites with immobilized antigens or antibodies or other ligand binding molecules such as aptamers, nucleic acids, etc. associated with a plurality of distinct febrile illnesses, all located in a test zone at a junction of the first and second sorbent materials. For purposes herein, the term "distinct" when used in conjunction with the words "flow path" or "migration path" shall be understood to mean "not in fluid communication except via a test zone". Where the test cell of the invention is provided in a housing, the housing is provided with a first opening adjacent the first location and a second opening adjacent the second location. A viewing window is provided in the housing above the test zone. In an embodiment, the first sorbent material and second sorbent material are separate pieces which overlie one another and the test line is printed on one or both of the sorbent materials at the junction. Alternatively, although not preferred, the first and second sorbent materials can be integral with each other. The systems of the invention preferably also include a control line or site which may be seen from the viewing window. According to an embodiment, the sorbent materials are laid out in a T shape, where the first location for receiving the buffer or buffer-conjugate solution is located near one end of the top bar of the T, the second location for receiving the sample is located near the end of the stem of the T, and the sorbent materials overlie each other at the intersection. Of course, the sorbent materials may be laid out in other configurations. The materials, thicknesses and lengths of the first and second sorbent materials are chosen to adjust the timing regarding the liquid sample and liquid buffer reaching the test site. In the dry conjugate system of the invention, a dry conjugate is provided between the first opening and the test site. The conjugate is supported on or within the sorbent material such that when a buffer is added in the first opening, the sorbent material wicks the buffer to the conjugate which is then carried by the buffer to the test site. In the liquid conjugate system of the invention, a buffer-conjugate liquid subsystem is provided and applied to the first opening. The sorbent material then wicks the buffer-conjugate subsystem to the test site.

According to a method of using the test cell, sample of interest is provided to the second opening or location and allowed to travel to the test site. If any antigens or antibodies are present in the sample, the antigens or antibodies will bind with respective ligand-binding molecules at an associated test line. After a desired amount of time to ensure the sample has traveled to the test site, a liquid such as a buffer solution is added to the first opening or location. If the sorbent material is supporting a conjugate (i.e., in a dry conjugate system), the liquid is preferably simply a buffer solution. If the sorbent material is not supporting a conjugate (i.e., in a liquid conjugate system), the liquid is preferably a buffer-conjugate liquid subsystem. In any event, after sufficient time to permit the conjugate to migrate to the test site (and control site if provided), the test site (and control site if provided) is inspected in order to determine whether the sample is "positive" or not. In a "positive" sample, conjugate have bound with each antigen or antibody attached at the test lines and associated with a respective one of the febrile illnesses. In a positive sample, at least one test line corresponding to at least febrile illness and the control line will be colored. In a negative sample, none of the test lines corresponding to a febrile illness is colored, but the control line is colored.

In accord with another embodiment of the assay test, the assay test includes three sorbent test materials, one to initially receive the diluted sample, and one each for the detection of different stage antibodies for a plurality of febrile illnesses. This expedites detection of one or more of the plurality of febrile illnesses at different stages of the illness, for example, within a few days after symptoms begin and later in a disease course or after recovery.

The assay test includes a test cell having a first buffer-receiving location which receives a buffer solution and a first sorbent material defining a first horizontal flow path for the first buffer solution, a second sorbent material defining a second horizontal flow path distinct from the first horizontal flow path for the same or a different buffer solution provided to the first buffer-receiving location or to a second buffer-receiving location, a third sorbent material defining a third horizontal flow path for a sample provided at a sample-receiving location, the third horizontal flow path being distinct from the first and second horizontal flow paths, a fourth flow path for the sample provided at the sample-receiving location, the fourth horizontal flow path being distinct from the first, second, and third horizontal flow paths, a first test site with a plurality of distinct and longitudinally displaced test lines with one of immobilized antigens or antibodies associated with distinct pathogenically unrelated febrile illnesses, preferably all located in a first test zone at a junction of the first and third sorbent materials, and a second test site with a plurality of distinct and longitudinally displaced test lines with one of immobilized antigens or antibodies associated with the distinct pathogenically unrelated febrile illnesses. In one embodiment, the first and second test sites includes immobilized antibodies or antigens that distinguish for different stages of the respective febrile illnesses, e.g., early and late stage detection. In another embodiment, the first test site include immobilized antibodies associated with the unrelated febrile illnesses, whereas the second test site include immobilized antigens associated with the unrelated febrile illnesses. The second test site is located in a second test zone at a junction of the second and fourth sorbent materials. For purposes herein, the term "distinct" when used in conjunction with the words "flow path" or "migration path" shall be understood to mean "not in fluid communication except either (i) via a test zone, or (ii) at a buffer receiving or sample receiving location".

Where the test cell of the invention is provided in a housing, the housing is provided with a first opening adjacent the first buffer-receiving location and a sample-receiving opening adjacent the sample receiving location. Where a second buffer-receiving location is utilized, a second buffer-receiving opening is provided in the housing adjacent the second buffer-receiving location. A first viewing window is provided in the housing above the first test line and a second viewing window is provided in the housing above the second test line.

In use, a reactive sample, and positive test, may include one of the first and second test windows indicating a positive reaction for only one or both of the stages of illness for one or more of the plurality of febrile illnesses. In the absence of the antigens or antibodies indicative of a stage of illness for the febrile illnesses of interest, no associated colored line would be observed under the test window area, and the test would be indicated as negative. The sample continues to migrate along the second and third sorbent materials and produces a colored line in each of the respective control areas of the first and second test windows to indicate that the sample and reagents have been properly applied and have migrated through the along the first, second and third second sorbent materials.

Other multi-assay test designs, provided with the requisite combination of antibodies or antigens, specific to antigens and/or antibodies associated with the plurality of febrile illnesses for which the test is designed can be used as well, including wet tests and other constructs.

The assay test is adapted to simply, quickly and accurately determine whether the carrier of a bodily fluid sample is the subject of one of plurality of a febrile illnesses. This allows important point-of-care decisions to be made before additional individual, regional, or even and global complications occur.

DETAILED DESCRIPTION OF THE PREFERRED EMBODIMENTS

Figure 1:
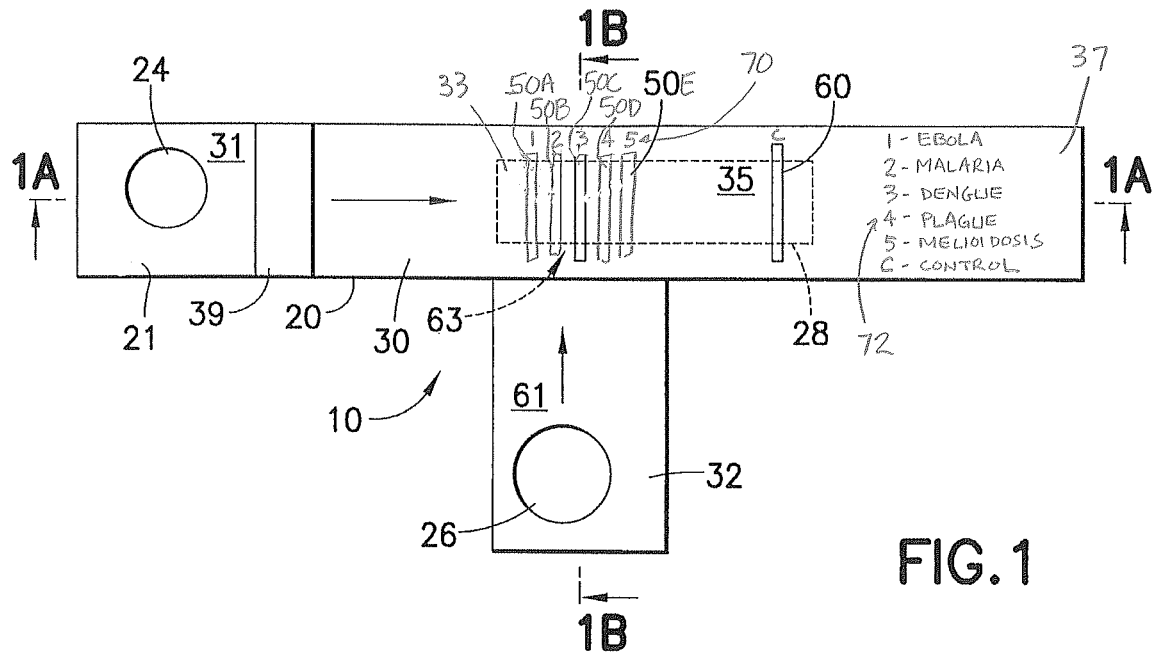
FIG. 1 is a top view of a first embodiment of an assay test for testing multiple unrelated febrile illnesses.
Figure 1A:
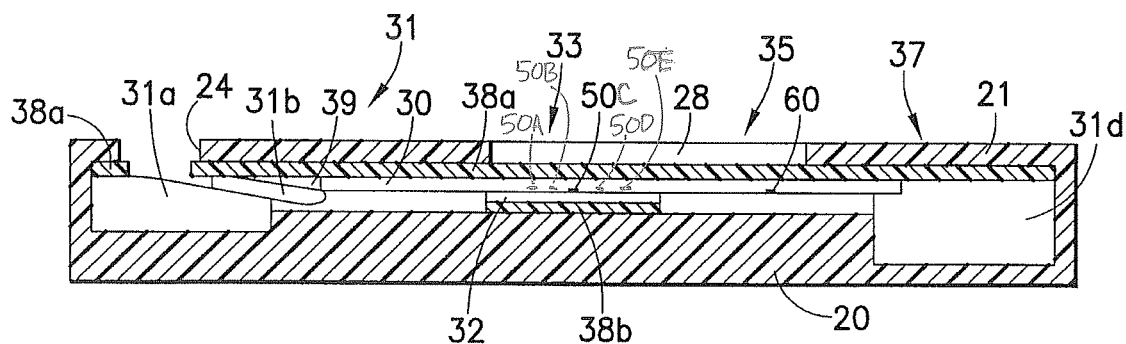
FIG. 1A is a section view across line 1A-1A in FIG. 1.
Figure 1B:
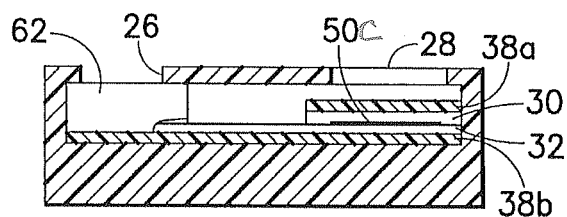
FIG. 1B is a section view across line 1B-1B in FIG. 1.

Turning now to FIGS. 1, 1A and 1B, a dual path lateral flow immunoassay device test cell 10 is provided and includes: a housing 20 having a top wall 21 defining first and second holes 24, 26, and a clear plastic window 28; and a carrier in the form of first and second sorbent or bibulous materials 30, 32 defining perpendicular horizontal flow paths in the housing. The first sorbent material 30 includes at least two and preferably three or four zones and may be made from a plurality of materials. A first zone 31 (sometimes called a filter zone) is located at the first hole 24 and extends to a second zone 33 (sometimes called a test zone) which is located at the junction of a "T". The first zone 31 may include a filter 31a, a pad 31b on or in which a plurality of conjugates having desired antigens or antibodies with attached colored markers are deposited and immobilized, and a first portion of a thin membrane or sorbent or bibulous material 30 typically made from nitrocellulose with a plastic backing (not shown). The first zone 31 is adapted to receive a buffer solution, to cause the buffer solution to contact the conjugate, thereby mobilizing the conjugate, and to wick the conjugate-carrying buffer solution to the second zone 33. The second (test) zone 33 includes a second portion of the thin membrane 30 which is preferably printed with a plurality of longitudinally displaced test lines 50A, 50B, 50C, 50D, 50E (collectively 50A-E) having immobilized antigens or antibodies (depending on whether the test cell is designed to test for the presence of antibodies or antigens) for unrelated febrile illnesses on the membrane. Indicia 70 are provided on the top wall 21 to associate the test lines with a key 72 identifying the respective febrile illnesses under test. The selection of the febrile illnesses for the associated immobilized antigens or antibodies positioned on respective test lines, is discussed in detail below. The test lines 50A-E may be seen through the window 28 provided in the housing. An optional third zone 35 (sometimes called a control zone)

which includes a third portion of the thin membrane 30 may also be printed with a control line 60 typically containing antibodies to the conjugate antigens (or in some cases antibodies which will bind to conjugate antibodies, or even antigens which will bind to conjugate antibodies) as is well known in the art. Where the third zone 35 is provided, the window 28 extends above the control line 60; alternatively a separate window may be provided for the control line. If desired, an optional fourth zone 37 (sometimes called a reservoir zone) may be provided as a wicking reservoir as is also well known in the art. The fourth zone 37 includes a relatively thicker absorbent paper 31d. In an embodiment, overlying all the zones is a thin, transparent plastic film or card 38a having an adhesive which keeps the sorbent materials in place. The card 38 may be cut with an opening at hole 24 so that it does not block liquid access to the hole 24.

The second sorbent material 32 may also be made from a plurality of materials and preferably includes two zones 61, 63. The first zone 61 (sometimes called a filter zone) includes a filter or pad 62 and a first portion of a thin membrane or sorbent or bibulous material 32 typically made from nitrocellulose with a backing (not shown). The first zone 61 is located at the second hole 26 and extends to the second zone 63. The second zone 63 includes a second portion of the thin membrane 32 which is in contact with the second zone 33 of the first sorbent material 30. As is seen in FIGS. 1A and 1B, the first sorbent material 30 overlies the second sorbent material 32 such that the membranes are in contact with each other (as opposed to the backings contacting the membranes or each other), and such that the test lines 50A-E are effectively located between the membranes, although in one embodiment the second sorbent material touches the first sorbent material at or adjacent the test lines, but does not overlie the test zones. Thus, test lines 50A-E could be printed on the second zone 63 of the second sorbent material 32 instead of, or in addition to the second zone 33 of the first sorbent material 30. If desired, a thin plastic film or card 38b having an adhesive which keeps the second sorbent material in place may be utilized. The sorbent materials may be in the form of strips and may be constructed from a standard-type nitrocellulose, and provided with different pore sizes to aid in the flow and migration of sample and solution, as described hereafter. Additional details and variations on the construction of the test cell, including materials, orientation and configuration of the sorbent material, shapes of the test cell housing, etc. are described in U.S. Pat. Nos. 7,189,522, 7,569,397, and 7,879, 597, all to Esfandiari, which are incorporated by reference herein in their entireties.

The immunoassay of FIGS. 1, 1A and 1B may be utilized as follows. First, a sample (not shown) possibly containing antibodies (or antigens) is provided to the second opening or hole 26 and allowed to migrate through the second sorbent material 32 to its second zone 63 which is in contact with the second zone 33 of the first sorbent material 30. The sample is preferably fingerstick whole blood. However, venous whole blood, serum, and/or plasma can similarly be used.

Optionally, after providing the sample into hole 26, a preferably measured amount of liquid such as a buffer solution may be added to hole 26 to help in the migration of the sample. Alternatively, the sample and buffer solution are premixed before being added into hole 26. Regardless, the sample reaches the test lines 50A-E which are printed atop the second zone 33 of the first sorbent material or infused therein. After a desired amount of time, by which time the antibodies (or antigens) in the sample (if present) will have had an opportunity to bind to the antigens (or antibodies) immobilized at the test lines 50A-E, a preferably measured amount of liquid such as a buffer solution (not shown) is added to the first opening 24. After another period of time, sufficient to permit the conjugate to migrate to the test lines 50A-E (and control site 60 if provided), the test lines 50A-E (and control site 60 if provided) are inspected via window 28 in order to determine whether the sample is "positive" or not for any of the febrile illnesses for which the test is adapted. Typically, a "positive" test indicating the presence of the antibody (or antigen) in the sample is obtained when both a test line of test lines 50A-E and the control site 60 show lines of color. A "positive" test will be indicative for only the febrile illness(es) associated with the colored test line(s). A "negative" test indicating the lack of the presence of the antibody (or antigen) in the sample is obtained when only the control site 60 shows a line of color; i.e., none of the test lines 50A-E show color.

Those skilled in the art will appreciate that the immunoassay 10 functions as follows. Because the test lines 50A-E are provided with antigens (or antibodies) for febrile illnesses immobilized on a membrane, if the test sample contains antibodies to the antigens (or antigens to the antibodies) for the respective febrile illnesses, the antibodies (or antigens) will bind themselves to the antigens (or antibodies) at the respective test line. Thereafter, when the conjugate 39 containing an antigen for the antibody (or antibody for the antigen) coupled to a colored marker is caused to migrate to the test lines 50A-E, if the test sample contains the antibodies (or antigens) which are now held at the test lines 50A-E, the antigen (or antibody) of the conjugate will bind itself to the antibodies (or antigens) and the colored marker will cause a colored line to appear at the respective lines 50A-E. If the test sample does not contain antibodies (or antigens), the conjugate will not have the antibodies (antigens) to bind to at the test lines 50A-E, and no colored line will appear at the test site. On the other hand, because the control line 60 is provided with antibodies (or antigens), the antigens (or antibodies) of the conjugate will always bind to the antibodies (or antigens) in the control line 60, thereby causing a colored line to appear at the control site 60 if the conjugate reaches the control site 60. Thus, if sufficient buffer solution is provided to the test cell, a colored line should always appear at the control site 60, thereby providing a control for the test.

Now, in accord with one aspect of the invention, the test lines 50A-E are adapted to indicate presence of one or more febrile illness selected from a plurality of unrelated febrile illnesses. The febrile illnesses indicated by test lines 50A-50E do not share any particularly common pathogen or other cause for their respective illness states, such that a positive detection of one illness is in no way presumptive, indicative or in any way etiologically related to a positive outcome for another of the febrile illnesses on the test.

In accord with an assay test described herein, the assay test is adapted to provide presumptive (i.e., confirmatory) detection of at least two unrelated febrile illnesses. In one embodiment, the assay test more preferably is adapted to provide presumptive detection of at least three unrelated febrile illnesses. The febrile illnesses can be selected for testing on the assay using one or more common features of (or alternatively dissimilar features relative to) the one or more of the unrelated febrile illnesses. By way of example, the selection of febrile illnesses for which the test is designed may include a illnesses caused by one or more of the following: distinct viruses, bacterium and/or parasites; infection from distinct viruses, bacterium, parasites or other contagions that are animal borne, whether selected to be animal borne by the same animal (mosquitoes) or by different animals (e.g., bat, rodent, mosquito, flea); infection from distinct viruses, bacterium, parasites, or other contagions that can be aerosolized for transmission; infection from viruses, bacterium, parasites or other contagions that are transmitted from direct contact; infection from viruses, bacterium, parasites or other contagions that are generally transmitted in the tropics and/or subtropics; infection from a virus, bacteria, parasite sharing one or more related features and which causes a febrile illness. The selection of febrile illness in a test may optionally include a set or subset of illnesses meeting any one or more criteria.

It is specifically recognized that the febrile illnesses tested by the assay test do not share any particularly common cause for their respective disease states. That is, there is no known pathogenic pattern, pathogenic causation, or other pathogenic relationship from one illness to the other. As such, to the extent the test provides a positive detection for one febrile illness, it is expected that only one positive detection for a febrile illness will be indicated on any one test. It is, of course, possible that a particular test sample, when tested, can provide positive detection of two or even more febrile illnesses. But given the lack of relationship of the febrile illnesses for which the test is administered, such results would not necessarily be expected or a part of the design of the test. Nonetheless, it is anticipated that the unrelated febrile illnesses which can be detected on any one test will nonetheless have a rationale in the arrangement by which they are together tested; i.e., to facilitate and expedite early detection and diagnosis of febrile illness at point of detection or point of care facility.

In accord with that aspect of the assay test, the febrile illnesses detected by the assay test may be linked by those febrile illnesses having a prevalence within a geographical proximity (by of example, within a state, or within a country, or within neighboring countries, or within proximate countries, or within a continent, or within a defined range of latitude, such as ±20° latitude about the equator, or as bounded by geological formations including rivers and/or mountains and/or valleys, or an geographical area subject to a common or like environmental conditions or a disaster, or geopolitical hardships, or other geographically definable boundary), and/or those febrile illnesses having a prevalence within a population in a given time period, and/or those febrile illnesses to which a group or population may be subject (by way of example, general population of western Africa, or aid workers of one or more relief organizations, whether localized or scattered, or inhabitants of one or more temporary or semi-permanent shelter or housing systems, including shelter or housing established by the United Nations or another relief aid organization), and/or those febrile illnesses which are potentially borne by travelers at a point of entry at a geographical location (e.g., air travelers at an airport or sea travelers at a sea port), and/or those febrile illnesses that may be potentially the subject to of a bioterror attack (e.g., can be transmitted in an aerosolized manner). For each of the potential groups identified above, an assay test may be designed to test for febrile illnesses that are appropriate for the circumstance. In accord with the invention, the febrile illnesses are unrelated illnesses, each having a different causative factor. In accord with the invention, it is possible that the unrelated febrile illnesses selected for a test may have a non-causal logical relationship.

By way of example, as shown in the key 72 on the assay test 10 of FIG. 1, the assay test can be designed to test for the Ebola Virus (which is a viral infection and can be animal borne), *Plasmodium* parasites (Malaria)(which is a parasitic infection and is animal borne by mosquito), Dengue virus (which is a viral infection and is animal borne by mosquito, as well as most common in tropical/subtropical geographical regions), *Yersinia pestis* (Plague)(which is a bacterial infection, is animal borne by rodent and their fleas, is specific to identified endemic regions, and can be in aerosol form), *Burkholderia pseudomallei* (Melioidosis)(which is a bacterial infection, a tropical illness, and can be in aerosol form or in contaminated soil). These febrile illnesses have no etiological relationship. A subset thereof are commonly bacterial infections: Pague and Medioidosis, though caused by different bacteria. A subset thereof are tropical: Dengue virus and Melioidosis, through caused by different agents. A subset thereof are animal borne: Ebola, Malaria, Dengue, and Plague, through borne by different animals (mosquito, rodent and fleas). A subset are distinguished as transmitted by different means: virus (Ebola, Dengue), bacteria (Plague, Melioidosis), and parasite (Malaria). From the foregoing, it appreciated that the febrile illnesses under test are unrelated. It is appreciated that another combination of unrelated febrile illnesses may be tested together, including a subset of the illnesses discussed above together with one or more of, by way of example, Anthrax, Lassa fever, Tularemia, Leptospirosis, Marburg hemorrhagic Fever, Rickettsial disease, Thyphoid, Chikungunya, *Coxiella burnetii* bacteria (Q-fever), Meningococcal, Pneomococcus, and Crimean-Congo haemorrhagic fever (CCHF).

In accord with embodiments of the assay, and not by way of limitation, the assay is adapted to detect for at least three of, or all of, Ebola Virus, *Plasmodium* parasites (Malaria), Dengue virus, as well as the bacteria *Yersinia pestis* (Plague) and *Burkholderia pseudomallei* (Melioidosis) in a bodily fluid. In accord with the preferred assay test, the assay is preferably adapted to use the bodily fluid of fingerstick whole blood, venous whole blood, serum and/or plasma.

Turning now to FIGS. 2A through 2E, another test cell 110 substantially similar to the test cell 10 is shown with like parts having related reference numerals. Test cell 10' includes a housing including a top shell 21'. The sorbent strips are preferably substantially arranged as described above in FIG. 1. The top shell 21' defines a first hole 24' in the form of a well for receiving a buffer (B) solution onto the first sorbent strip 30', and a second hole 26' in the form of a well for receiving a mixture of the sample and buffer solution (S+B) onto the second sorbent strip 32'. The first sorbent strip 30' is marked with five test lines (marked "1 2 3 4 5" on the shell 21'), each test line corresponding to one of the antigens (or antibodies) for one of the unrelated febrile illnesses under test. Strip 30' also includes another line functioning as a control line (marked C). The test lines are provided with a color dye (e.g., blue) so that they are visible. The control line is provided with a color dye (e.g., green) so that it is visible. A first window 35a' is provided in the housing over the test lines and a second window 35b' is provided in the housing over the control line; however such window may be combined in a communal opening.

Figure 2B:
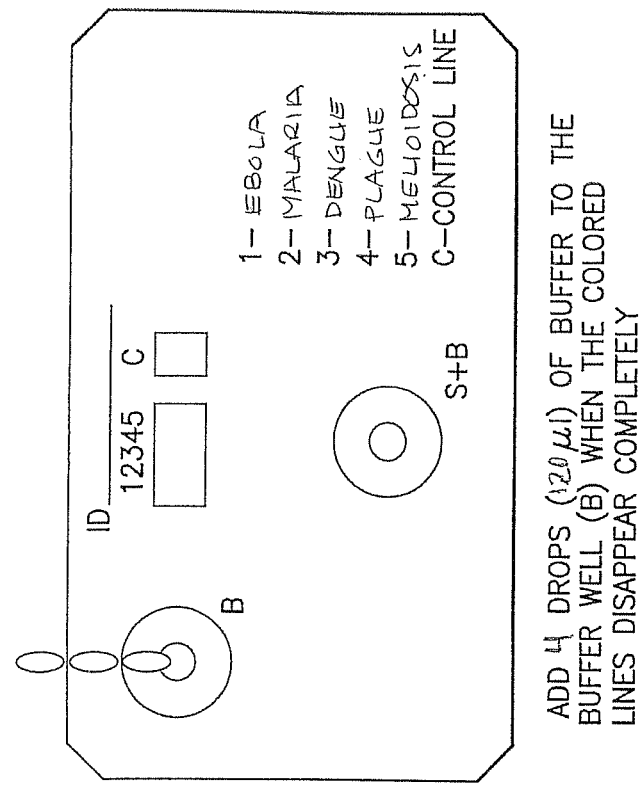
FIGS. 2A-2E illustrate use of a febrile illness test.
Figure 2A:
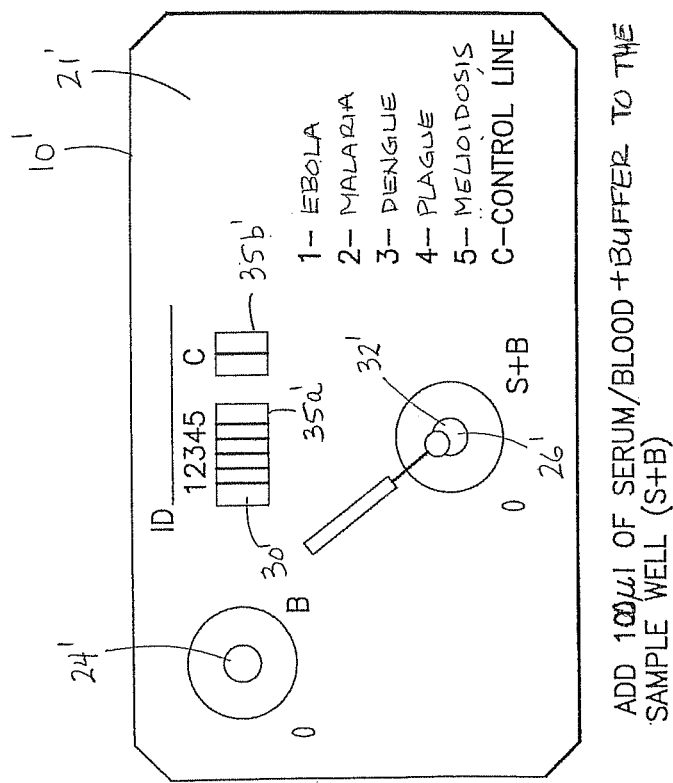
Figure 2C:
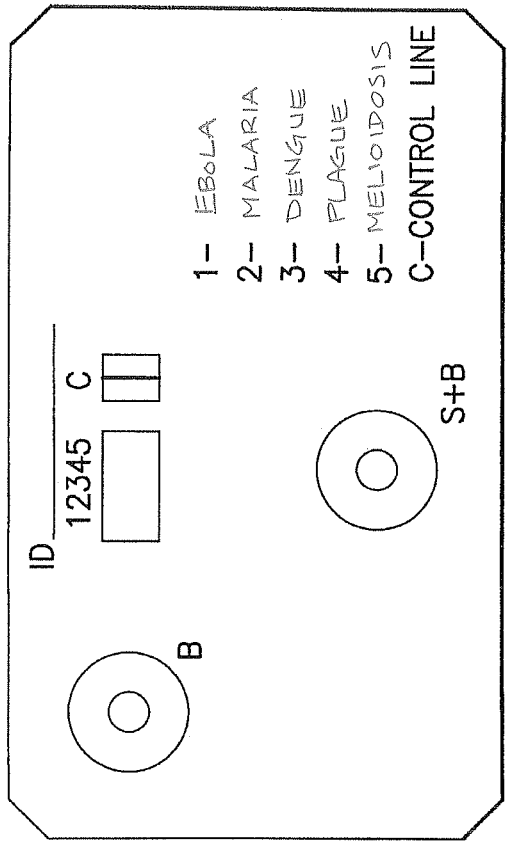
Figure 2E:
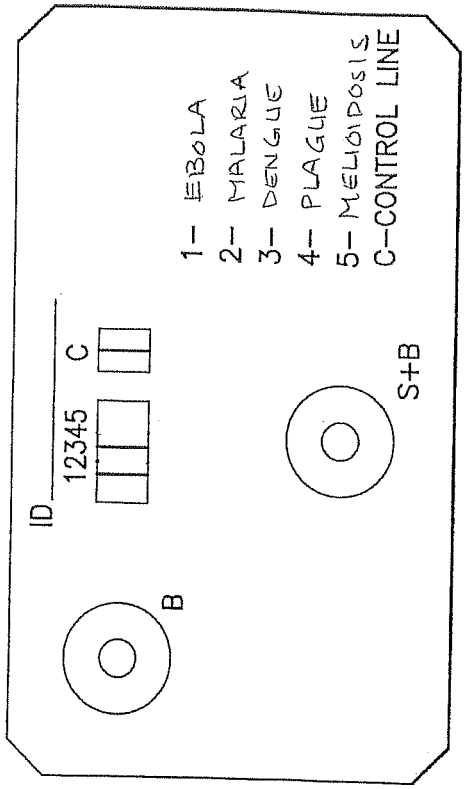
Figure 2D:
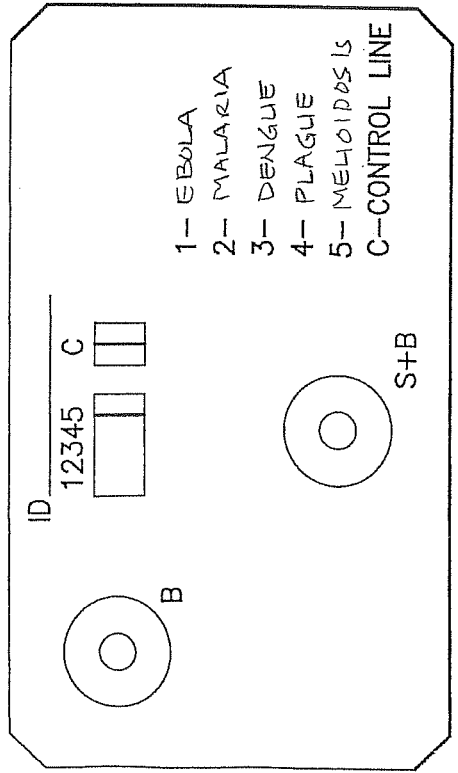

In operation, fingerstick whole blood or other suitable bodily fluid sample is obtained and mixed with buffer solution. Then, referring to FIG. 2B, approximately 100 µl of blood and buffer mixture is added to the same sample well (marked S+B). Migration of the sample (typically with the help of the buffer) to the test zone will cause the dye at all the test lines and as well as the control line to dissipate. Disappearance of the dye from the lines confirms that the sample has reached the test area. Once the lines have completely disappeared, as shown at FIG. 2B, approximately 120 μl of buffer is added to the buffer opening (marked B) in order to cause migration of a conjugate marker to the test area. After a period of time, typically 20 minutes, results may be read. In FIG. 2C, only the control line C is seen, thereby indicating a valid result and that the sample tested negatively for each of the febrile illnesses for which the sample was tested; in this case Ebola, Malaria, Dengue, Plague, and Melioidosis. In FIG. 2D, the control line and line 5 are seen, thereby indicating a valid result that the sample tested positively for Melioidosis antibodies, but negatively for the antibodies for Ebola, Malaria, Dengue, and Plague. In FIG. 2E, the control line and lines 1 and 3 are seen, thereby indicating a presumed unusual but nonetheless valid result: the sample tested positive for Ebola and Dengue antibodies, but negatively for the antibodies for Malaria, Plague, and Melioidosis. It is noted that if the control line C is not seen, the test results are not interpreted as being valid.

Turning now to FIGS. 3A-3D, another embodiment of a multiple unrelated febrile illness test 110 is shown. The test cell includes a first test strip 130a having a fluid pathway along which a test site 150a printed. The test site 150a has multiple test lines (1 2 3 4 5) and a control line (C). The first strip 130a also has a liquid buffer receiving portion 124a, and immobilized conjugates 139a that are released to migrate along the fluid pathway and toward the test site when the liquid receiving portion receives a liquid solution, all such features substantially as described as with respect to sorbent material 30 in the embodiment described in FIGS. 1, 1A and 1B. The test lines of the test site 150a on the first test strip 130a are adapted to test for antibodies (or antigens) for an EARLY (first) stage of a plurality of febrile illnesses. As such, and by way of example, in an embodiment a test line is provided that detects IgM antibodies to the antigen of Ebola, which can be used to confirm early stages of Ebola; i.e., within a few days after the symptoms begin.

The test 110 also includes a second test strip 130b, substantially similar to and displaced from the first test strip, and having a second test site 150b. The test lines at the second test site 150b are adapted to test for antibodies (or antigens) for a LATE (second) stage of the plurality of febrile illnesses. By way of example, in an embodiment, the LATE stage test strip is adapted to detect IgG antibodies to the antigen of Ebola which can be used to confirm a later course of the disease, or even indicate that recovery is occurring. The detection of IgG and IgM antibodies to the antigens of Ebola is described in U.S. Pat. No. 7,189,522, previously incorporated by reference herein.

A third sorbent strip 170 extends between the first and second sorbent strips 130a, 130b, and contacts the first and second strips at the respective test sites 150a, 150b of the first and second strips. The third sorbent strip 170 includes a zone 172 in which to receive a common sample and buffer (S+B) that feeds to the test sites 150a, 150b of the first and second test strips 130a, 130b. It is appreciated that the first, second and third strips can be distinctly formed from each other, or alternatively may be constructed as unitary member.

Figure 3A:
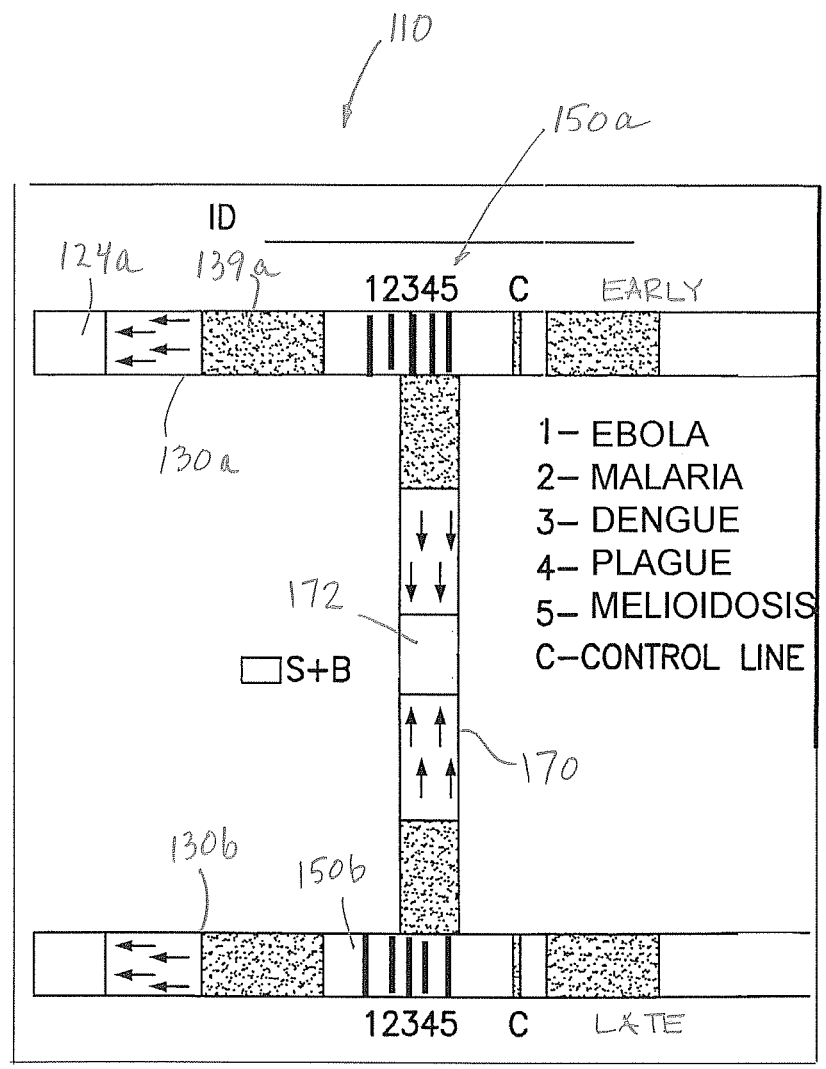
FIGS. 3A-3E described another embodiment of a febrile illness test, adapted to test for different stages of multiple febrile illnesses.
Figure 3B:
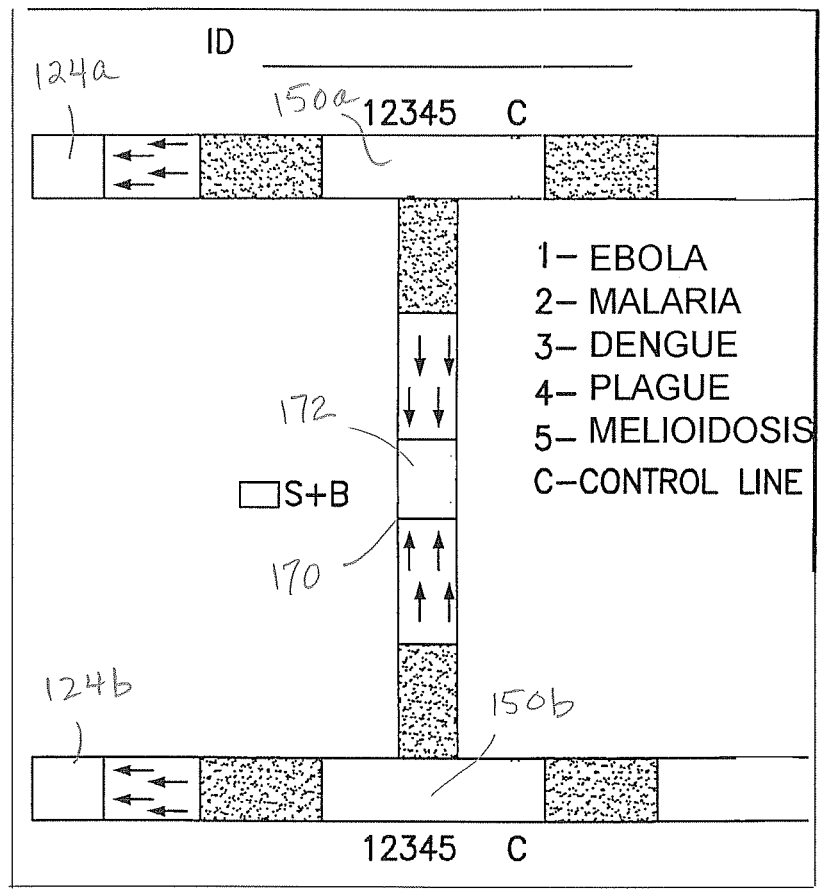
Figure 3C:
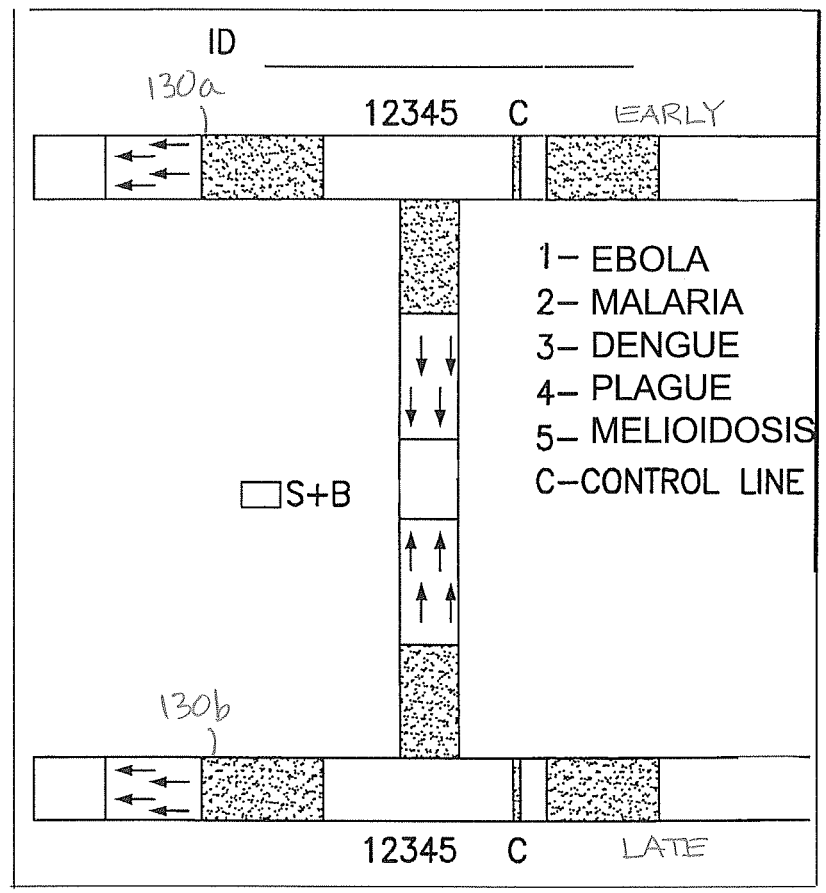
Figure 3D:
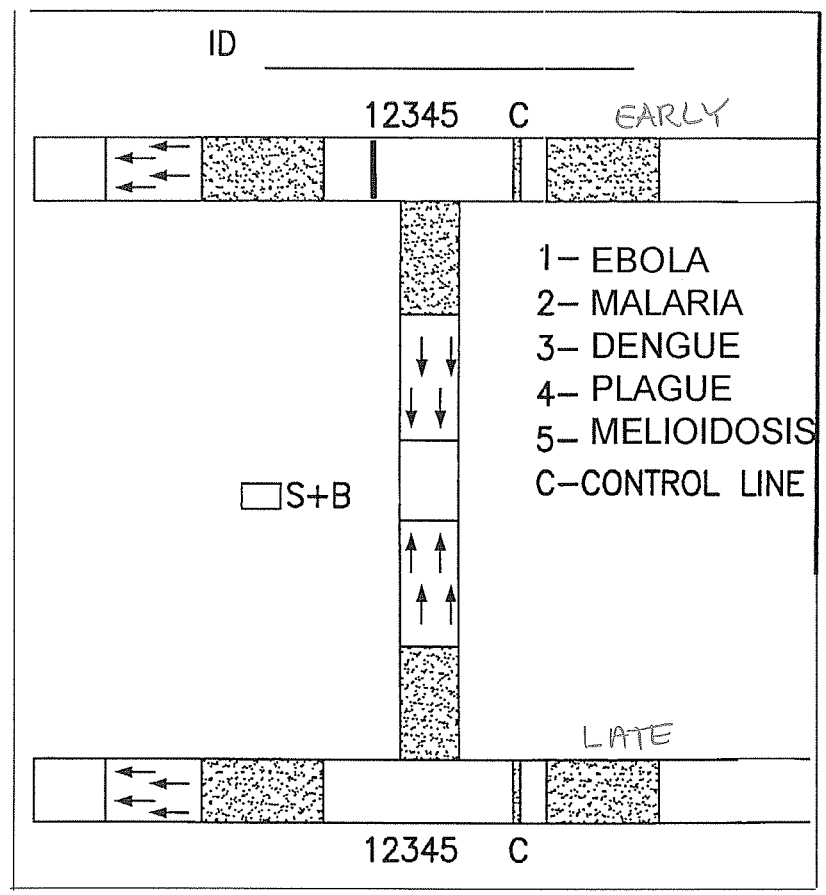
Figure 3E:
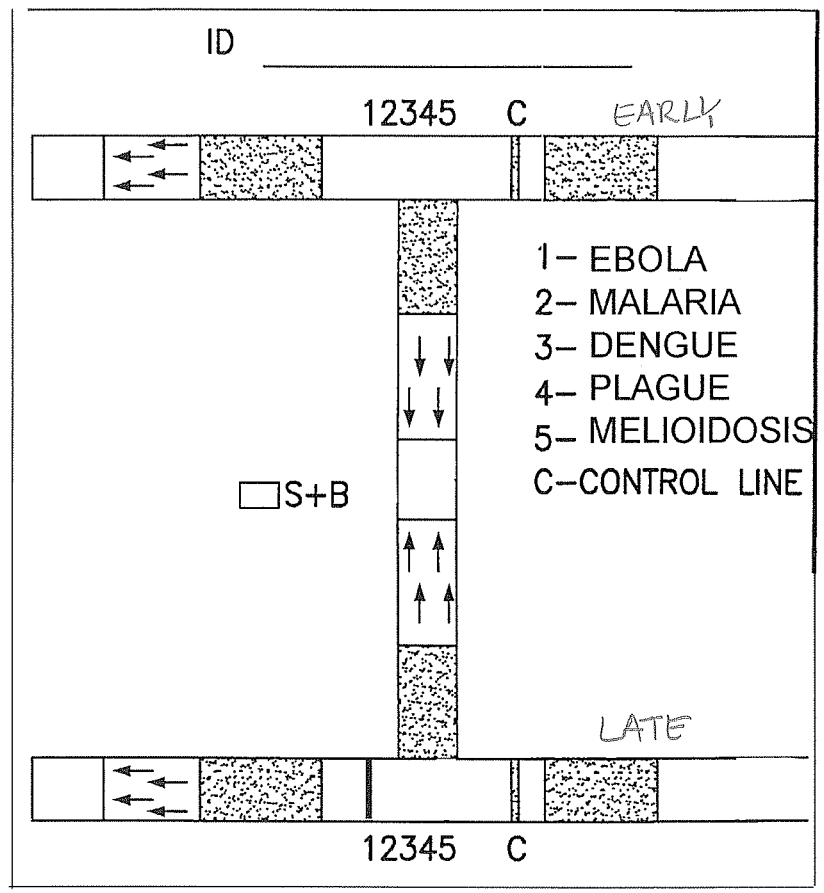

In use, fingerstick whole blood or other suitable bodily fluid sample is obtained and mixed with buffer solution. Then, referring to FIG. 3A, preferably approximately 100 μl of blood and buffer mixture is added to the same sample well zone 172 (marked S+B) marked between the arrows. The sample, with the help of the buffer, migrates in opposite directions away from sample well toward the first and second test sites 150a, 150b. Referring to FIG. 3B, once the lines have completely disappeared, preferably approximately 120 μl of buffer is added to each of the buffer liquid receiving area 124a, 124b in order to cause migration of the conjugate markers on the first and second strips toward the respective test sites 150a, 150b. After a period of time, typically 20 minutes, results may be read. In FIG. 3C, only the control line C is seen in each of the first and second test strips 130a, 130b, thereby indicating a valid result and that the sample tested negatively for each stage of each of the febrile illnesses for which the sample was tested; in this case Ebola, Malaria, Dengue, Plague, and Melioidosis. In FIG. 3D, along the EARLY stage detection first test strip, the control line and line 1 are seen, thereby indicating a valid result that the sample tested positively for early stage of Ebola; along the LATE stage detection second test strip, the control line and no test line are seen, thereby indicating a valid result and no later stage illness state detectable for any of the illnesses. In FIG. 3E, along the EARLY detection test strip 130a, the control line and no test lines are seen, thereby indicating a valid result without detection of the early stage of any of the illnesses. In FIG. 3E, along the LATE stage detection test strip 130b, the control line and line 1 are seen, thereby indicating a valid result and detection of late stage, and possibly a recovery stage, of Ebola. The test is negative for the antibodies for Malaria, Dengue, Plague, and Melioidosis.

Figure 4:
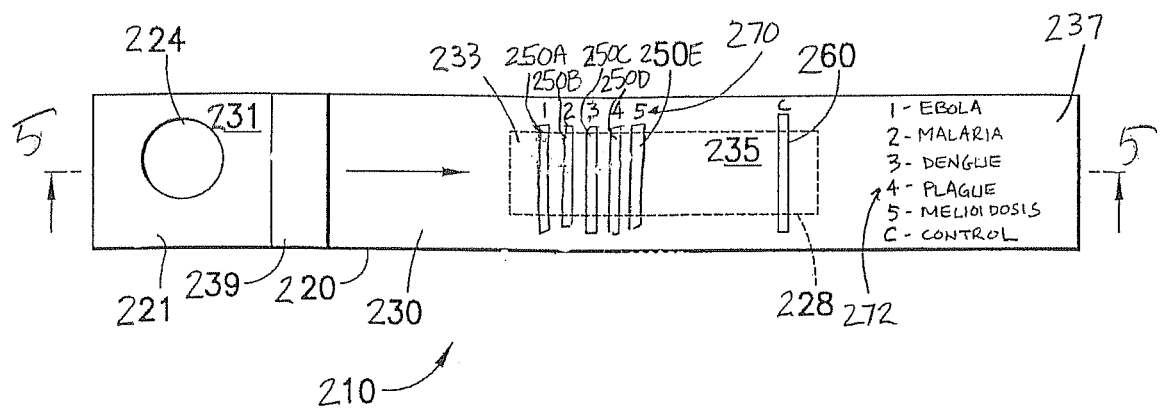
FIG. 4 is a top view of another embodiment of a febrile illness test.
Figure 5:
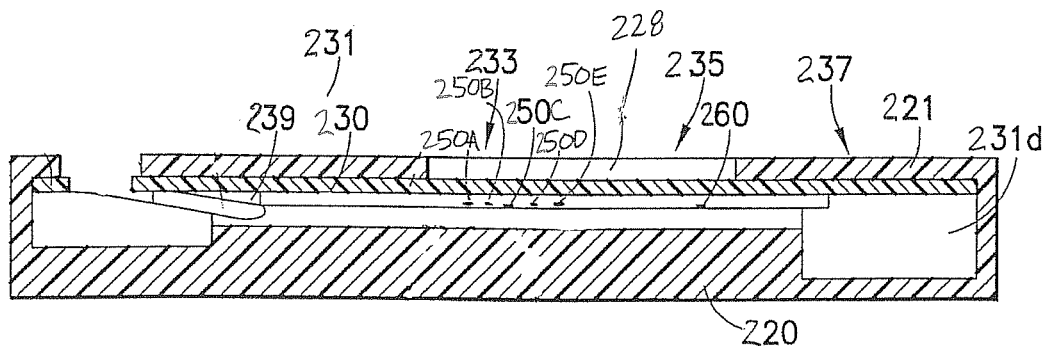
FIG. 5 is a section view through line 5-5 of FIG. 4.

Turning now to FIGS. 4 and 5, a lateral flow immunoassay device test cell 210 is provided for the presumptive detection of infection with one or more selected unrelated febrile illnesses, to either verify or reject the respective illnesses individually. The test cell 210 has a housing 220 having a top wall 221 defining a first hole 224, a sorbent or bibulous material 230 defining a horizontal flow path in the housing. The sorbent material 230 includes a plurality of zones preferably made of a plurality of materials. In one zone, conjugates 239 having desired antigens or antibodies with attached colored markers are deposited and immobilized. The antigens are respectively associated with several independent and unrelated febrile illnesses, as previously described. The first zone 231 is adapted to receive a sample and buffer solution through the first hole 224, to cause the sample and buffer solution to contact the conjugate 239 thereby mobilizing the conjugate, and to wick the conjugate-carrying sample and buffer solution to the second zone 233. The second (test) zone 233 is preferably printed with a plurality of longitudinally displaced test lines 250A-E at which are immobilized antigens or antibodies (depending on whether the test cell is designed to test for the presence of antibodies or antigens) as is well known in the art. A window 228 of clear plastic is preferably provided over the test lines 250A-E. Indicia 270, 272 are provide to associate the test line 250A-E with the respective illnesses under test. Additional zones may be provided to the test to aid in movement, binding, wicking, solution/fluid reception, solution/fluid storage, or viewing of the test lines. An optional third zone 35 (sometimes called a control zone) may also be printed with a control line 260 typically containing antibodies to the conjugate antigens (or in some cases antibodies which will bind to conjugate antibodies, or even antigens which will bind to conjugate antibodies) as is well known in the art. Where the third zone 235 is provided, the window 228 of preferably extends above the control line 260. If desired, an optional fourth zone 237 (sometimes called a reservoir zone) may be provided as a wicking reservoir as is also well known in the art. The fourth zone 237 includes a relatively thicker absorbent paper 241d.

As yet another alternative, test lines for both early and later stage forms of a febrile illness can be co-located on a common test strip or sorbent material, such that each of the early and later stage forms can be presumptively confirmed on a single test strip. By way of example, early and later stage forms of three unrelated febrile illness can be tested with a test zone having six test lines, and early and later stage forms of five unrelated febrile illness can be tested with a test zone having ten test lines on a single strip.

The antigens are respectively associated with unrelated, epidemiologically independent febrile illnesses. The febrile illnesses share a common condition of a high grade fever, and potentially additional considerations. The febrile illnesses are epidemiologically independent as each illness does not share a common biological factor in its cause. However, it may be advisable to test for the febrile illnesses together to confirm one of a potential identity of febrile illnesses, or alternatively collectively rule out all such febrile illnesses, at one time.

There have been described and illustrated herein several embodiments of immunoassays and methods of their use. While particular embodiments of the invention have been described, it is not intended that the invention be limited thereto, as it is intended that the invention be as broad in scope as the art will allow and that the specification be read likewise. Thus, while the specification discusses ligand binding using antigen/antibody reactions, other ligand binding mechanisms such as aptamer binding, nucleic acid binding, enzymatic binding, etc. may also be used. Also, while the test cells are described as having various numbers of lines for testing for a corresponding number of ligands, it will be appreciated that different numbers of lines may be utilized for testing for different numbers of ligands. In such a case, a single housing may be utilized with a single hole for the sample, or alternatively, multiple holes could be utilized if desired. Where multiple holes are utilized, multiple strips may be used for one or more samples provided. Preferably, the multiple strips would touch (e.g., overlie or underlie) a single strip providing a migration path for the conjugate. It may also be possible to provide a single hole which sits over or leads to two adjacent strips adapted for sample migration. Further, while the test cells are described as having holes in the top wall of a housing for receiving the sample and the buffer-solution or buffer-conjugate subsystem, it will be appreciated that one or both holes may be provided in the end wall or side wall of the housing. Moreover, while it is preferred that the test utilized a lateral flow format with a bibulous material as a carrier, it is appreciated that other test constructs, including those using a different solid state carrier or even a liquid carrier, can be utilized to perform the tests described herein as well.

Also, while the test cell is described is being utilized in conjunction with a sample of fingerstick whole blood, it is appreciated that other bodily fluid can be used as well in the test cell, including venous whole blood, serum and/or plasma. Additionally, the assay test can be adapted for saliva, vomit, urine, fecal matter, or other bodily discharge, each of which is considered a bodily fluid for purposes herein. It is appreciated that depending upon the sample an appropriate diluent or other additive may need to be combined with the bodily fluid to allow the bodily fluid to properly migrate on the sorbent material and otherwise be reactant within the test.

Those skilled in the art will also appreciate that the housing may be modified in additional ways to include separate windows for each test line. Also, while the invention was described in conjunction with the use of a buffer solution which is added to the migration path of the conjugate and optionally to the migration path of the sample, it will be appreciated that that one or more buffers may be chosen as desired to be added to the migration paths depending upon the test or tests to be conducted. Thus, buffers such as phosphate buffers or TRIS (tris hydroxymethylaminomethane) buffers are often utilized. However, the invention is intended to encompass the use of any diluent including water. In addition, the diluent may, if needed, may be added to and mixed with the sample prior to adding the sample to the sorbent material or the sample may be deposited first and the diluent may be added thereafter. Likewise, any diluent capable of causing conjugate to migrate may be utilized, and may be premixed with the conjugate in a liquid conjugate system, or provided to the migration path for the conjugate in a dry conjugate system. It will therefore be appreciated by those skilled in the art that yet other modifications could be made to the provided invention without deviating from its spirit and scope as claimed.

What is claimed is:

1. A test device for the qualitative detection from a liquid sample of at least one febrile illness from a plurality of pathogenically unrelated febrile illnesses, the test device for use with a solution, the device comprising:
   a) a first sorbent material having a first width and a first length substantially longer than said first width, the first sorbent material having a plurality of conjugates having antigens or antibodies with attached visible color markers deposited thereon, and having a first location for receiving the solution and defining a first migration path for the solution and conjugates;
   b) a second sorbent material having a second width and a second length substantially longer than said second width, the second sorbent material separate from the first sorbent material and defining a second migration path separate from the first migration path, the second sorbent material having a second location for receiving the liquid sample;
   c) a test site located on or in the first sorbent material or on or in the second sorbent material and having a plurality of separately located immobilized ligand-binding mechanisms for receiving the liquid sample, each ligand-binding mechanism being capable of binding with a ligand corresponding to one of the pathogenically unrelated febrile illnesses, wherein said plurality of separately located immobilized ligand-binding mechanisms includes a first mechanism that binds to a viral infection antigen or antibody, and a second mechanism that binds to a bacterial infection antigen or antibody or to a parasitic infection antigen or antibody, said viral infection antigen or antibody and said bacterial or parasitic infection antigen or antibody respectively corresponding to a first febrile illness and a second febrile illness that are prevalent within a geographical proximity, wherein the second sorbent material intersects the first sorbent material at or adjacent the test site, and
      wherein time is required for the liquid sample to laterally flow from the second location to the test site such that the liquid sample does not immediately wet the test site upon application; and
   d) a single control line spaced from said test site and having anti-conjugate antibodies such that said plurality of conjugates will bind to said anti-conjugate antibodies at said single control line.

2. The test device according to claim 1, wherein:
said second mechanism that binds to a bacterial infection antigen or antibody or to a parasitic infection antigen or antibody binds to a bacterial infection antigen or antibody.

3. The test device according to claim 2, wherein:
said plurality of separately located immobilized ligand-binding mechanisms includes a third mechanism that binds to a parasitic antigen or antibody.

4. The test device according to claim 1, wherein:
at least two ligand-binding mechanisms of said plurality of separately located immobilized ligand-binding mechanisms include mechanisms that bind to antigens or antibodies caused by at least two febrile illnesses that are animal borne by different animals.

5. The test device according to claim 4, wherein:
at least one of the febrile illnesses is borne by at least one of a bat, a rodent, a mosquito, and a flea, and at least another of the febrile illnesses is borne by a different animal.

6. The test device according to claim 1, wherein:
at least one ligand-binding mechanism of said plurality of separately located immobilized ligand-binding mechanisms includes a mechanism that binds to antigens or antibodies caused by a febrile illness that can be transmitted by an aerosolized pathogenic agent.

7. The test device according to claim 1, wherein:
at least one ligand-binding mechanism of said plurality of separately located immobilized ligand-binding mechanisms includes a mechanism that binds to antigens or antibodies caused by a febrile illness that can be transmitted by direct contact.

8. The test device according to claim 1, wherein:
at least one ligand-binding mechanism of said plurality of separately located immobilized ligand-binding mechanisms includes a mechanism that binds to antigens or antibodies caused by a febrile illness that is a tropical and/or subtropical illness.

9. The test device according to claim 3, wherein:
at least two of said first, second, and third mechanisms bind to antigens or antibodies caused by at least two febrile illnesses that are animal borne by different animals.

10. The test device according to claim 9, wherein:
at least two of said first, second, and third mechanisms bind to antigens or antibodies caused by at least two different febrile illnesses prevalent in a common geographical region.

11. The test device according to claim 9, wherein:
said at least two of said first, second, and third mechanisms that bind to antigens or antibodies caused by at least two different febrile illnesses prevalent in a common geographical region include at least one caused by a febrile illness that can be transmitted through air and at least one caused by a febrile illness that can be transmitted by direct contact.

12. The test device according to claim 1, wherein:
said first mechanism that binds to a viral infection antigen or antibody binds to an antigen or antibody resulting from one of an Ebola Virus, Lassa fever virus, Chikungunya virus, Marburg hemorrhagic fever virus, Meningococcal virus, and Crimean-Congo haemorrhagic fever (CCHF) virus, and said second mechanism that binds to a bacterial infection antigen or antibody or to a parasitic infection antigen or antibody, binds to an antigen or antibody resulting from one of Malaria (parasite), Plague bacteria, Melioidosis bacteria, Anthrax bacteria, Tularemia bacteria, Leptospirosis bacteria, Rickettsial disease bacteria, Typhoid bacteria, Q-fever bacteria, Meningococcal bacteria, and Pneumococcus bacteria.

13. The test device according to claim 1, wherein:
said first mechanism that binds to a viral infection antigen or antibody binds to an antigen or antibody resulting from one of an Ebola Virus and Dengue virus, and said second mechanism that binds to a bacterial infection antigen or antibody or to a parasitic infection antigen or antibody, binds to an antigen or antibody resulting from one of Malaria (parasite), Plague bacteria, and Melioidosis bacteria.

14. The test device according to claim 1, wherein:
at least one of said first mechanism and said second mechanism is capable of binding to bioterrorism pathogens.

15. The test device according to claim 1, wherein:
said plurality of separately located immobilized ligand-binding mechanisms includes a first mechanism that binds to a Malaria antigen or antibody, a second mechanism that binds to a Dengue antigen or antibody, and a third mechanism that binds to an Ebola antigen or antibody.

16. The test device according to claim 1, wherein:
said plurality of separately located immobilized ligand-binding mechanisms includes a first mechanism that binds to a Malaria antigen or antibody, a second mechanism that binds to a Dengue antigen or antibody, and a third mechanism that binds to a Melioidosis antigen or antibody.

* * * * *